(12) United States Patent
Rasmussen

(10) Patent No.: US 6,762,040 B2
(45) Date of Patent: Jul. 13, 2004

(54) METHOD FOR INCREASING GENE COPY NUMBER IN A HOST CELL AND RESULTING HOST CELL

(75) Inventor: Michael Dolberg Rasmussen, Vallensbæk (DK)

(73) Assignee: Novozymes A/S, Bagsvaærd (DK)

(*) Notice: Subject to any disclaimer, the term of this patent is extended or adjusted under 35 U.S.C. 154(b) by 0 days.

(21) Appl. No.: 09/869,855

(22) PCT Filed: May 23, 2001

(86) PCT No.: PCT/DK01/00356
§ 371 (c)(1),
(2), (4) Date: Jul. 5, 2001

(87) PCT Pub. No.: WO01/90393
PCT Pub. Date: Nov. 29, 2001

(65) Prior Publication Data
US 2003/0044940 A1 Mar. 6, 2003

Related U.S. Application Data
(60) Provisional application No. 60/208,052, filed on May 30, 2000.

(51) Int. Cl.⁷ .............................. C12P 1/00; C12N 15/00
(52) U.S. Cl. ............... 435/69.1; 435/41; 435/71.1; 435/71.2; 435/440; 435/471; 435/476; 435/477; 435/479; 435/481; 435/485; 435/243; 435/252.1; 435/252.3; 435/252.31; 435/252.5; 435/320.1

(58) Field of Search ................ 435/41, 69.1, 71.1, 435/71.2, 440, 471, 476, 477, 479, 481, 485, 320.1, 243, 252.1, 252.3, 252.31, 252.5; 536/23.1, 24.1

(56) References Cited

U.S. PATENT DOCUMENTS

5,435,730 A        7/1995   Adams et al.
2003/0032186 A1 *  2/2003   Jorgensen et al. ........... 435/455

FOREIGN PATENT DOCUMENTS

EP     0 965 641      12/1999
WO     WO 00/09705    2/2000

* cited by examiner

Primary Examiner—James Ketter
Assistant Examiner—David Lambertson
(74) Attorney, Agent, or Firm—Elias Lambiris

(57) ABSTRACT

The invention relates to a method for increasing the copy number of a chromosomally integrated expression cassette in a microbial strain without leaving antibiotic resistance markers behind in the strain, the necessary genetic constructs, and the strains resulting from the method of the invention.

30 Claims, 1 Drawing Sheet

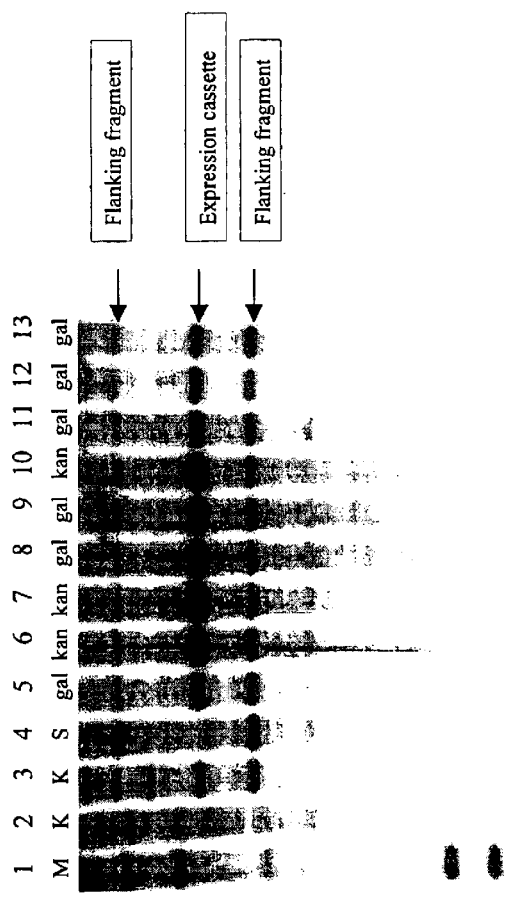

Southern analysis on different amplified clones.
Numbers in parenthesis refer to the clone numbers in table 1.

Lane 1: Marker, Lambda-HindIII digest
Lane 2: PL1801
Lane 3: Two copy strain
Lane 4: Singlecopy strain (#2)
Lane 5: Multicopy by galactose (#9)
Lane 6: Multicopy by kanamycine (#13)
Lane 7: Multicopy by kanamycine (#14)
Lane 8: Multicopy by galactose (#15)
Lane 9: Multicopy by galactose (#17)
Lane 10: Multicopy by kanamycine (#19)
Lane 11: Multicopy by galactose (#21)
Lane 12: Multicopy by galactose (#25)
Lane 13: Multicopy by galactose (#27)

SEQUENCE LISTING

<160> NUMBER OF SEQ ID NOS: 12

<210> SEQ ID NO 1
<211> LENGTH: 6405
<212> TYPE: DNA
<213> ORGANISM: Artificial Sequence
<220> FEATURE:
<223> OTHER INFORMATION: Synthetic

<400> SEQUENCE: 1

```
ctaaatcggt agaagcccaa acgttccacg atgcgatttg tgcccttatc gtagaagagc      60
tgtttgaata tgcaggcaaa tggcgtaata ttcgtgtgca aggaccgaca acatttctac     120
catccttgac tgtacaggta gcaatggcag gtgccatgtt gattggtctg catcatcgca     180
tctgttatac gacgagcgct tcggtcttaa ctgaagcagt taagcaatca gatcttcctt     240
caggttatga ccatctgtgc cagttcgtaa tgtctggtca actttccgac tctgagaaac     300
ttctggaatc gctagagaat ttctggaatg ggattcagga gtggacagaa cgacacggat     360
atatagtgga tgtgtcaaaa cgcataccat tttgaacgat gacctctaat aattgttaat     420
catgttggag ctcagtgaga gcgaagcgaa cacttgattt tttaattttc tatcttttat     480
aggtcattag agtatactta tttgtcctat aaactattta gcagcataat agatttattg     540
aataggtcat ttaagttgag catattagag gaggaaaatc ttggagaaat atttgaagaa     600
cccgagaatg gaggccttct caattgagaa ggccttttt aaagaacaag ggtgcctaaa      660
caggcaccct tgttagctgt tatttgattt tcacaataac atcattactg aatttttagtt     720 tccaagtgcc ttttgcataa gcttccttgt caacttcaaa tgcttttaca cctgttactt     780
taatattagg atttagatca ctcaaaattt tagagttatc aacttttgtc tcagttgcat     840
agtttacaga agcatcaata tcagaatcat aagaagtacc atcagcatca actaatttaa     900
cagttggaat tgaaaagag ctaatcggct ttttagatac gtttttaatt gtatattgaa      960
cagctacaat tgtacctcag cggcgcagcg ggtcgacgcg gccgcaacca tttgatcaaa    1020
gcttgcatgc ctgcaggtcg attcacaaaa aataggcaca cgaaaaacaa gttaagggat    1080
```

-continued

```
gcagtttatg catcccttaa cttacttatt aaataattta tagctattga aaagagataa    1140
gaattgttca aagctaatat tgtttaaatc gtcaattcct gcatgtttta aggaattgtt    1200
aaattgattt tttgtaaata ttttcttgta ttctttgtta acccatttca taacgaaata    1260
attatacttt tgtttatctt tgtgtgatat tcttgatttt tttctactta atctgataag    1320
tgagctattc actttaggtt taggatgaaa atattctctt ggaaccatac ttaatataga    1380
aatatcaact tctgccatta aaagtaatgc caatgagcgt tttgtattta ataatctttt    1440
agcaaacccg tattccacga ttaaataaat ctcattagct atactatcaa aaacaatttt    1500
gcgtattata tccgtactta tgttataagg tatattacca tatattttat aggattggtt    1560
tttaggaaat ttaaactgca atatatcctt gtttaaaact tggaaattat cgtgatcaac    1620
aagtttattt tctgtagttt tgcataattt atggtctatt tcaatggcag ttacgaaatt    1680
acacctcttt actaattcaa gggtaaaatg gccttttcct gagccgattt caaagatatt    1740
atcatgttca tttaatctta tatttgtcat tattttatct atattatgtt ttgaagtaat    1800
aaagttttga ctgtgtttta tattttctc gttcattata accctcttta atttggttat    1860
atgaattttg cttattaacg attcattata accacttatt ttttgtttgg ttgataatga    1920
actgtgctga ttacaaaaat actaaaaatg cccatatttt ttcctcctta taaaattagt    1980
ataattatag cacgagctct gataaaatg aacatgatga gtgatcgtta aatttatact    2040
gcaatcggat gcgattattg aataaaagat atgagagatt tatctaattt cttttttctt    2100
gtaaaaaaag aaagttctta aaggttttat agttttggtc gtagagcaca cggtttaacg    2160
acttaattac gaagtaaata agtctagtgt gttagacttt atgaaatcta tatacgttta    2220
tatatattta ttatccggag gtgtagcatg tctcattcaa ttttgagggt tgccagagtt    2280
aaaggatcaa gtaatacaaa cgggatacaa agacataatc aaagagagaa taaaaactat    2340
aataataaag acataaatca tgaggaaaca tataaaaatt atgatttgat taacgcacaa    2400
aatataaagt ataagataaa aattgatgaa acgattgatg agaattattc agggaaacgt    2460
aaaattcggt cagatgcaat tcgacatgtg gacggactgg ttacaagtga taaagatttc    2520
tttgatgatt taagcggaga agaaatagaa cgattttta aagatagctt ggagtttcta    2580
gaaaatgaat acgtaagga aaatatgctg tatgcgactg tccatctgga tgaaagagtc    2640
ccacatatgc actttggttt tgtccctta acagaggacg ggagattgtc tgcaaaagaa    2700
cagttaggca acaagaaaga ctttactcaa ttacaagata gatttaatga gtatgtgaat    2760
gagaaaggtt atgaacttga aagaggcacg tccaaagagg ttacagaacg agaacataaa    2820
gcgatggatc agtacaagaa agatactgta tttcataaac aggaactgca agaagttaag    2880
gatgagttac agaaggcaaa taagcagtta cagagtggaa tagagcatat gaggtctacg    2940 aaacccttg attatgaaaa tgagcgtaca ggtttgttct ctggacgtga agagactggt    3000
agaaagatat taactgctga tgaatttgaa cgcctgcaag aaacaatctc ttctgcagaa    3060
cggattgttg atgattacga aaatattaag agcacagact attacacaga aaatcaagaa    3120
ttaaaaaaac gtagagagag tttgaaagaa gtagtgaata catggaaaga ggggtatcac    3180 gaaaaagta aagaggttaa taaattaaag cgagagaatg atagtttgaa tgagcagttg    3240
aatgtatcag agaaatttca agctagtaca gtgactttat atcgtgctgc gagggcgaat    3300
ttccctgggt ttgagaaagg gtttaatagg cttaaagaga aattctttaa tgattccaaa    3360
tttgagcgtg tgggacagtt tatggatgtt gtacaggata atgtccagaa ggtcgataga    3420
```

```
aagcgtgaga acacagcgtac agacgattta gagatgtaga ggtacttta tgccgagaaa    3480
acttttgcg tgtgacagtc cttaaaatat acttagagcg taagcgaaag tagtagcgac    3540
agctattaac tttcggtttc aaagctctag gatttttaat ggacgcagcg catcacacgc    3600
aaaaaggaaa ttggaataaa tgcgaaattt gagatgttaa ttaaagacct ttttgaggtc    3660
tttttttctt agattttggg ggttatttag gggagaaaac ataggggggt actacgacct    3720
cccccctagg tgtccattgt ccattgtcca acaaataaa taaatattgg gttttaatg     3780
ttaaaggtt gtttttatg ttaaagtgaa aaaacagat gttgggaggt acagtgatgg      3840
ttgtagatag aaaagaagag aaaaagttg ctgttacttt aagacttaca acagaagaaa    3900
atgagatatt aaatagaatc aaagaaaaat ataatattag caaatcagat gcaaccggta   3960
ttctaataaa aaaatatgca aaggaggaat acggtgcatt taaacaaaa aaagatagac    4020
agcactggca tgctgcctat ctatgactaa attttgttaa gtgtattagc accgttatta   4080
tatcatgagc gaaaatgtaa taaagaaac tgaaaacaag aaaaattcaa gaggacgtaa    4140
ttggacattt gtttatatc cagaatcagc aaaagccgag tggttagagt atttaaaaga   4200
gttacacatt caatttgtag tgtctccatt acatgatagg gatactgata cagaaggtag  4260
gatgaaaaaa gagcattatc atattctagt gatgtatgag ggtaataat cttatgaaca   4320
gataaaaata attacagaag aattgaatgc gactattccg cagattgcag gaagtgtgaa  4380
aggtcttgtg agatatatgc ttcacatgga cgatcctaat aaatttaaat atcaaaaga   4440
agatatgata gtttatggcg gtgtagatgt tgatgaatta ttaaagaaaa caacaacaga  4500
tagatataa ttaattaaag aaatgattga gtttattgat gaacaaggaa tcgtagaatt   4560
taagagttta atggattatg caatgaagtt taaatttgat gattggttcc cgcttttatg  4620
tgataactcg gcgtatgtta ttcaagaata tataaaatca aatcggtata atctgaccg    4680
atagattttg aatttaggtg tcacaagaca ctctttttc gcaccagcga aaactggttt    4740
aagccgactg cgcaaaagac ataatcgact ctagaggatc cttttagtcc agctgatttc   4800
acttttgca ttctacaaac tgcataactc atatgtaaat cgctccttt taggtggcac     4860
aaatgtgagg cattttcgct cttccggca accacttcca agtaaagtat aacacactat   4920
actttatatt cataaagtgt gtgctctgcg aggctgtcgg cagtgccgac caaaaccata  4980
aaacctttaa gacctttctt tttttacga gaaaaaagaa acaaaaaaac ctgccctctg    5040
ccacctcagc aaaggggggt tttgctctcg tgctcgttta aaaatcagca agggacaggt   5100
agtatttttt gagaagatca ctcaaaaaat ctccaccttt aaacccttgc caattttat   5160
tttgtccgtt ttgtctagct taccgaaagc cagactcagc aagaataaaa ttttattgt   5220
ctttcggttt tctagtgtaa cggacaaaac cactcaaaat aaaaaagata caagagaggt  5280
ctctcgtatc ttttattcag caatcgcgcc cgattgctga acagattaat aatgagccgc   5340
gggtgaggaa agacaggact tgatgataca agggcaaaac agctttgctt caccgcttgc  5400
gggaagcaac gatccaaagg tgattcacca gtattgcggg ccgacaccgc ctgacaagga  5460
tcatgcgtat acattgacgg tctatgcttt agatgctgag ctgaatcttc agccgggctt  5520
ttacttgaat gagctctatc aagaaatgaa agagcacatt cttgctgaaa cctctatcga  5580
attgctggca agggtttaag ctaaaaaata tgaaaaaact attaataaac gattaaactt  5640
cttaaaaatg gatgtggacc ggttctgaat tctgatcaaa tggttcagtg agagcgaagc  5700
gaacacttga ttttttaatt ttctatcttt tataggtcat tagagtatac ttatttgtcc  5760
tataaactat ttagcagcat aatagattta ttgaataggt catttaagtt gagcatatta  5820
```

| | |
|---|---|
| gaggaggaaa atcttggaga aatatttgaa gaacccgaac gcgtgagtag ttcaacaaac | 5880 |
| gggccagttt gttgaagatt agatgctata attgttatta aaaggattga aggatgctta | 5940 |
| ggaagacgag ttattaatag ctgaataaga acggtgctct ccaaatattc ttatttagaa | 6000 |
| aagcaaatct aaaattatct gaaaagggaa tgagaatagt gaatggacca ataataatga | 6060 |
| ctagagaaga aagaatgaag attgttcatg aaattaagga acgaatattg gataaatatg | 6120 |
| gggatgatgt taaggctatt ggtgtttatg gctctcttgg tcgtcagact gatgggccct | 6180 |
| attcggatat tgagatgatg tgtgtcatgt caacagagga agcagagttc agccatgaat | 6240 |
| ggacaaccgg tgagtggaag gtggaagtga attttgatag cgaagagatt ctactagatt | 6300 |
| atgcatctca ggtggaatca gattggccgc ttacacatgg tcaattttc tctattttgc | 6360 |
| cgatttatga ttcaggtgga tacttagaga aagtgtatca aactg | 6405 |

<210> SEQ ID NO 2
<211> LENGTH: 5943
<212> TYPE: DNA
<213> ORGANISM: Artificial Sequence
<220> FEATURE:
<223> OTHER INFORMATION: Synthetic

<400> SEQUENCE: 2

| | |
|---|---|
| gatccatctg aaggtcgata cggggatgaa cagacttggt gtaaaacag aggaagaagt | 60 |
| tcagaacgtg atggcaattc ttgaccgcaa ccctcgttta aagtgcaaag gggtatttac | 120 |
| ccattttgcg acagcggatg aaaaagaaag aggctatttc ttaatgcagt ttgagcgctt | 180 |
| taaagagctg attgctccgc tgccgttaaa gaatctaatg gtccactgcg cgaacagcgc | 240 |
| cgctggactc cggctgaaaa aaggcttttt taatgcagtc agattcggca tcggcatgta | 300 |
| tggccttcgc ccgtctgctg acatgtcgga cgagataccg tttcagctgc gtccggcatt | 360 |
| taccctgcat tcgacactgt cacatgtcaa actgatcaga aaaggcgaga gcgtcagcta | 420 |
| cggagccgag tacacagcgg aaaaagacac atggatcggg acggtgcctg taggctatgc | 480 |
| ggacggctgg ctccgaaaat tgaaagggac cgacatcctt gtgaagggaa aacgcctgaa | 540 |
| aattgccggc cgaatttgca tggaccaatt tatggtggag ctggatcagg aatatccgcc | 600 |
| gggcacaaaa gtcacattaa taggccggca ggggatgaa tatatttcca tggatgagat | 660 |
| tgcaggaagg ctcgaaacca ttaactatga ggtggcctgt acaataagtt cccgtgttcc | 720 |
| ccgtatgttt ttggaaaatg ggagtataat ggaagtaaga atccttat tgcaggtaaa | 780 |
| tataagcaat taacttacct aaatggagaa ttcataaaac agctttgcgt cgacgatgaa | 840 |
| gatggatttt ctattattgc aatgtggaat tgggaacgga aaaattattt tattaaagag | 900 |
| tagttcaaca aacgggccag tttgttgaag attagatgct ataattgtta ttaaaaggat | 960 |
| tgaaggatgc ttaggaagac gagttattaa tagctgaata agaacggtgc tctccaaata | 1020 |
| ttcttattta gaaaagcaaa tctaaaatta tctgaaaagg gaatgagaat agtgaatgga | 1080 |
| ccaataataa tgactagaga agaaagaatg aagattgttc atgaaattaa ggaacgaata | 1140 |
| ttggataaat atggggatga tgttaaggct attggtgttt atggctctct tggtcgtcag | 1200 |
| actgatgggc cctattcgga tattgagatg atgtgtgtca tgtcaacaga ggaagcagag | 1260 |
| ttcagccatg aatggacaac cggtgagtgg aaggtggaag tgaattttga tagcgaagag | 1320 |
| attctactag attatgcatc tcaggtggaa tcagattggc cgcttacaca tggtcaattt | 1380 |
| ttctctattt tgccgattta tgattcaggt ggatacttag agaaagtgta tcaaactgct | 1440 |

-continued

```
aaatcggtag aagcccaaac gttccacgat gcgatttgtg cccttatcgt agaagagctg   1500
tttgaatatg caggcaaatg cgtaatatt cgtgtgcaag gaccgacaac atttctacca   1560
tccttgactg tacaggtagc aatggcaggt gccatgttga ttggtctgca tcatcgcatc   1620
tgttatacga cgagcgcttc ggtcttaact gaagcagtta agcaatcaga tcttccttca   1680
ggttatgacc atctgtgcca gttcgtaatg tctggtcaac tttccgactc tgagaaactt   1740
ctggaatcgc tagagaattt ctggaatggg attcaggagt ggacagaacg acacggatat   1800
atagtggatg tgtcaaaacg cataccattt tgaacgatga cctctaataa ttgttaatca   1860
tgttggttac gtatttatta acttctccta gtattagtaa ttatcatggc tgtcatggcg   1920
cattaacgga ataaagggtg tgcttaaatc gggccatttt cgctaataag aaaaaggatt   1980
aattatgagc gaattgaatt aataataagg taatagattt acattagaaa atgaaggggg   2040
attttgcggc cgccaacctc gagatctctt agattttgg ggttatttag gggagaaaac   2100 atagggggt actacgacct cccccctagg tgtccattgt ccattgtcca aacaaataaa   2160
taaatattgg gttttaatg ttaaaaggtt gttttttatg ttaaagtgaa aaaacagat   2220 gttgggaggt acagtgatgg ttgtagatag aaaagaagag aaaaaagttg ctgttacttt   2280
aagacttaca acagaagaaa atgagatatt aaataggaat tcgagctcat tattaatctg   2340
ttcagcaatc gggcgcgatt gctgaataaa agatacgaga gacctctctt gtatcttttt   2400
tattttgagt ggttttgtcc gttacactag aaaaccgaaa gacaataaaa attttattct   2460
tgctgagtct ggctttcggt aagctagaca aaacggacaa aataaaaatt ggcaagggtt   2520
taaaggtgga gattttttga gtgatcttct caaaaaatac tacctgtccc ttgctgattt   2580
ttaaacgagc acgagagcaa aaccccccctt tgctgaggtg gcagagggca ggttttttg   2640 tttcttttt ctcgtaaaaa aagaaaggt cttaaaggtt ttatggtttt ggtcggcact   2700
gccgacagcc tcgcagagca cacactttat gaatataaag tatagtgtgt tatactttac   2760
ttggaagtgg ttgccggaaa gagcgaaaat gcctcacatt tgtgccacct aaaaaggagc   2820
gatttacata tgagttatgc agtttgtaga atgcaaaaag tgaaatcagc tggactaaaa   2880
ggcagagctc ggtacccggg agctctatca attggtaact gtatctcagc ttgaagaagt   2940
gaagaagcag agaggctatt gaataaatga gtagaagcgc catatcggcg ctttctttt   3000 ggaagaaaat ataggggaaaa tggtacttgt taaaaattcg gaatatttat acaatatcat   3060 atgttcacaca ttgaaaggggg aggagaatca tgaaacaaca aaaacggctt tacgcccgat   3120
tgctgacgct gttatttgcg ctcatcttct tgctgcctca ttctgcagcc gcggcacacc   3180
ataatggtac gaacggcaca atgatgcagt actttgaatg gtatctacca aatgacggaa   3240
accattggaa tagattaagg tctgatgcaa gtaacctaaa agataaaggg atctcagcgg   3300
tttggattcc tcctgcatgg aagggtgcct ctcaaaatga tgtgggtat ggtgcttatg   3360 atctgtatga tttaggagaa ttcaatcaaa aggaaccat tcgtacaaaa tatggaacgc   3420
gcaatcagtt acaagctgcg gttaacgcct tgaaaagtaa tggaattcaa gtgtatggcg   3480
atgttgtaat gaatcataaa gggggagcag acgctaccga aatggttagg gcagttgaag   3540
taaacccgaa taatagaaat caagaagtgt ccggtgaata caattgag cttggacaa   3600 agtttgactt tccaggacga ggtaatactc attcaaactt caaatggaga tggtatcact   3660
ttgatggagt agattgggat cagtcacgta agctgaacaa tcgaatttat aaatttagag   3720
gtgatggaaa agggtgggat tgggaagtcg atacagaaaa cggtaactat gattacctaa   3780
tgtatgcaga tattgacatg gatcacccag aggtagtgaa tgagctaaga aattggggtg   3840
```

```
tttggtatac gaatacatta ggccttgatg gttttagaat agatgcagta aaacatataa    3900
aatacagctt tactcgtgat tggattaatc atgttagaag tgcaactggc aaaaatatgt    3960
ttgcggttgc ggaattttgg aaaaatgatt taggtgctat tgaaaactat ttaaacaaaa    4020
caaactggaa ccattcagtc tttgatgttc cgctgcacta taacctctat aatgcttcaa    4080
aaagcggagg gaattatgat atgaggcaaa tatttaatgg tacagtcgtg caaagacatc    4140
caatgcatgc tgttacattt gttgataatc atgattcgca acctgaagaa gctttagagt    4200
cttttgttga agaatggttc aaaccattag cgtatgcttt gacattaaca cgtgaacaag    4260
gctacccttc tgtatttat ggagattatt atggcattcc aacgcatggt gtaccagcga    4320
tgaaatcgaa aattgacccg attctagaag cgcgtcaaaa gtatgcatat ggaagacaaa    4380
atgactactt agaccatcat aatatcatcg gttggacacg tgaagggaat acagcacacc    4440
ccaactccgg tttagctact atcatgtccg atggggcagg aggaaataag tggatgtttg    4500
ttgggcgtaa taaagctggt caagtttgga ccgatatcac tggaaatcgt gcaggtactg    4560
ttacgattaa tgctgatgga tggggtaatt tttctgtaaa tggaggatca gtttctattt    4620
gggtaaacaa ataagtcgac ggcccagccg gccgagctcg gatagaagag cagagaagac    4680
ggatttcctg aaggaaatcc gtttttttat tttgcccgtc ttataaattt ctttgattac    4740
attttataat taattttaac aaagtgtcat aagcccgatg gaatattgct gaagcttatc    4800
gataacaggt cattttttag gagggtttac atcatggcaa tacttgttac tggcggtgcc    4860
ggttacattg gcagccacac atgtgttgaa ctattgaaca gcggctacga gattgttgtt    4920
cttgataatc tgtccaacag ttcagctgaa gcgctgaacc gtgtcaagga gattacagga    4980
aaagatttaa cgttctacga gcggattta ttggaccggg aagcggtaga ttccgttttt    5040
gctgaaaatg aaatcgaagc tgtgattcat tttgcagggt taaaagcagt cggcgaatct    5100
gtggcgattc ccctcaaata ttatcataac aatttgacag gaacgtttat tttatgcgag    5160
gccatggaga aatacggcgt caagaaaatc gtattcagtt catctgcgac agtatacggc    5220
gttccggaaa catcgccgat tacgaagac tttccattag cgcgacaaa tccttatggg    5280
cagacgaagc tcatgcttga acaaatattg cgtgatttgc atacagccga caatgagtgg    5340
agcgttgcgc tgcttcgtta ctttaacccg ttcggcgcgc atccaagcgg acggatcggt    5400
gaagacccga acggaatccc aaataacctt atgccgtatg tggcacaggt agcagtcggg    5460
aagctcgagc aattaagcgt attcggaaat gactatccga caaagacgg acaggcgta    5520
cgcgattata ttcacgtcgt tgatctcgca gaaggccacg tcaaggcgct ggaaaaagta    5580
ttgaactcta caggagccga tgcatacaac cttggaacag gcacaggcta cagcgtgctg    5640
gaaatggtca agcctttga aaagtgtca gggaagagg ttccataccg ttttgcggac    5700
cgccgtccgg gagacatcgc cacatgcttt gcagatcctg cgaaagccaa gcagaaacta    5760
ggctgggaag cgaaacgcgg ccttgaggaa atgtgtgctg attcctggag atggcagtct    5820
tctaatgtga atgggtataa gagtgcggaa taagaatgga ggccttctca attgagaagg    5880
ccttttttaa agaacaaggg tgcctaaaca ggcacccttg ttagctgtta tttgatttc    5940
acg                                                                 5943

<210> SEQ ID NO 3
<211> LENGTH: 5793
<212> TYPE: DNA
<213> ORGANISM: Artificial Sequence
<220> FEATURE:
```

<223> OTHER INFORMATION: Synthetic

<400> SEQUENCE: 3

| | | | | | |
|---|---|---|---|---|---|
| gatccatctg | aaggtcgata | cggggatgaa | cagacttggt | gtaaaaacag | aggaagaagt | 60 |
| tcagaacgtg | atggcaattc | ttgaccgcaa | ccctcgttta | aagtgcaaag | gggtatttac | 120 |
| ccattttgcg | acagcggatg | aaaaagaaag | aggctatttc | ttaatgcagt | ttgagcgctt | 180 |
| taaagagctg | attgctccgc | tgccgttaaa | gaatctaatg | gtccactgcg | cgaacagcgc | 240 |
| cgctggactc | cggctgaaaa | aaggcttttt | taatgcagtc | agattcggca | tcggcatgta | 300 |
| tggccttcgc | ccgtctgctg | acatgtcgga | cgagataccg | tttcagctgc | gtccggcatt | 360 |
| taccctgcat | tcgacactgt | cacatgtcaa | actgatcaga | aaggcgaga | gcgtcagcta | 420 |
| cggagccgag | tacacagcgg | aaaaagacac | atggatcggg | acggtgcctg | taggctatgc | 480 |
| ggacggctgg | ctccgaaaat | tgaagggac | cgacatcctt | gtgaagggaa | aacgcctgaa | 540 |
| aattgccggc | cgaatttgca | tggaccaatt | tatggtggag | ctggatcagg | aatatccgcc | 600 |
| gggcacaaaa | gtcacattaa | taggccggca | gggggatgaa | tatatttcca | tggatgagat | 660 |
| tgcaggaagg | ctcgaaacca | ttaactatga | ggtggcctgt | acaataagtt | cccgtgttcc | 720 |
| ccgtatgttt | ttggaaaatg | ggagtataat | ggaagtaaga | aatcctttat | tgcaggtaaa | 780 |
| tataagcaat | taacttacct | aaatggagaa | ttcataaaac | agctttgcgt | cgacgatgaa | 840 |
| gatggatttt | ctattattgc | aatgtggaat | tgggaacgga | aaaattattt | tattaaagag | 900 |
| tagttcaaca | aacgggccag | tttgttgaag | attagatgct | ataattgtta | ttaaaaggat | 960 |
| tgaaggatgc | ttaggaagac | gagttattaa | tagctgaata | agaacggtgc | tctccaaata | 1020 |
| ttcttattta | gaaaagcaaa | tctaaaatta | tctgaaaagg | gaatgagaat | agtgaatgga | 1080 |
| ccaataataa | tgactagaga | agaaagaatg | aagattgttc | atgaaattaa | ggaacgaata | 1140 |
| ttggataaat | atggggatga | tgttaaggct | attggtgttt | atggctctct | tggtcgtcag | 1200 |
| actgatgggc | cctattcgga | tattgagatg | atgtgtgtca | tgtcaacaga | ggaagcagag | 1260 |
| ttcagccatg | aatggacaac | cggtgagtgg | aaggtggaag | tgaattttga | tagcgaagag | 1320 |
| attctactag | attatgcatc | tcaggtggaa | tcagattggc | cgcttacaca | tggtcaattt | 1380 |
| ttctctattt | tgccgattta | tgattcaggt | ggatacttag | agaaagtgta | tcaaactgct | 1440 |
| aaatcggtag | aagcccaaac | gttccacgat | gcgatttgtg | cccttatcgt | agaagagctg | 1500 |
| tttgaatatg | caggcaaatg | gcgtaatatt | cgtgtgcaag | gaccgacaac | atttctacca | 1560 |
| tccttgactg | tacaggtagc | aatggcaggt | gccatgttga | ttggtctgca | tcatcgcatc | 1620 |
| tgttatacga | cgagcgcttc | ggtcttaact | gaagcagtta | agcaatcaga | tcttccttca | 1680 |
| ggttatgacc | atctgtgcca | gttcgtaatg | tctggtcaac | tttccgactc | tgagaaactt | 1740 |
| ctggaatcgc | tagagaattt | ctggaatggg | attcaggagt | ggacagaacg | acacggatat | 1800 |
| atagtggatg | tgtcaaaacg | cataccattt | tgaacgatga | cctctaataa | ttgttaatca | 1860 |
| tgttggttac | gtatttatta | acttctccta | gtattagtaa | ttatcatggc | tgtcatggcg | 1920 |
| cattaacgga | ataaagggtg | tgcttaaatc | gggccatttt | cgctaataag | aaaaaggatt | 1980 |
| aattatgagc | gaattgaatt | aataataagg | taatagattt | acattagaaa | atgaaagggg | 2040 |
| attttgcggc | cgccaacctc | gagatctctt | agatttttgg | ggttatttag | gggagaaaac | 2100 |
| ataggggggt | actacgacct | ccccccctagg | tgtccattgt | ccattgtcca | aacaaataaa | 2160 |
| taaatattgg | gtttttaatg | ttaaaaggtt | gttttttatg | ttaaagtgaa | aaaaacagat | 2220 |
| gttgggaggt | acagtgatgg | ttgtagatag | aaaagaagag | aaaaaagttg | ctgttacttt | 2280 |

-continued

```
aagacttaca acagaagaaa atgagatatt aaataggaat tcgagctcat tattaatctg      2340
ttcagcaatc gggcgcgatt gctgaataaa agatacgaga gacctctctt gtatcttttt      2400
tattttgagt ggttttgtcc gttacactag aaaaccgaaa gacaataaaa attttattct      2460
tgctgagtct ggctttcggt aagctagaca aaacggacaa aataaaaatt ggcaagggtt      2520
taaaggtgga gattttttga gtgatcttct caaaaaatac tacctgtccc ttgctgattt      2580
ttaaacgagc acgagagcaa accccccctt tgctgaggtg gcagagggca ggttttttg       2640 tttcttttt ctcgtaaaaa aaagaaaggt cttaaaggtt ttatggtttt ggtcggcact       2700
gccgacagcc tcgcagagca cacactttat gaatataaag tatagtgtgt tatactttac     2760
ttggaagtgg ttgccggaaa gagcgaaaat gcctcacatt tgtgccacct aaaaaggagc      2820
gatttacata tgagttatgc agtttgtaga atgcaaaaag tgaaatcagc tggactaaaa      2880
ggcagagctc ggtacccggg agctctatca attggtaact gtatctcagc ttgaagaagt      2940
gaagaagcag agaggctatt gaataaatga gtagaagcgc catatcggcg cttttctttt      3000
ggaagaaaat atagggaaaa tggtacttgt taaaaattcg gaatatttat acaatatcat      3060
atgttacaca ttgaaagggg aggagaatca tgaaacaaca aaaacggctt tacgcccgat      3120
tgctgacgct gttatttgcg ctcatcttct tgctgcctca ttctgcagcc gcggcacacc      3180
ataatggtac gaacggcaca atgatgcagt actttgaatg gtatctacca aatgacggaa      3240
accattggaa tagattaagg tctgatgcaa gtaacctaaa agataaaggg atctcagcgg      3300
tttggattcc tcctgcatgg aagggtgcct ctcaaaatga tgtgggggtat ggtgcttatg     3360 atctgtatga tttaggagaa ttcaatcaaa aaggaaccat tcgtacaaaa tatgaacgc       3420 gcaatcagtt acaagctgcg gttaacgcct tgaaaagtaa tggaattcaa gtgtatggcg      3480
atgttgtaat gaatcataaa gggggagcag acgctaccga aatggttagg gcagttgaag      3540
taaacccgaa taatagaaat caagaagtgt ccggtgaata tacaattgag gcttggacaa      3600
agtttgactt tccaggacga ggtaatactc attcaaactt caaatggaga tggtatcact      3660
ttgatggagt agattgggat cagtcacgta agctgaacaa tcgaatttat aaatttagag      3720
gtgatggaaa agggtgggat tgggaagtcg atacagaaaa cggtaactat gattacctaa      3780
tgtatgcaga tattgacatg gatcacccag aggtagtgaa tgagctaaga aattggggtg      3840
tttggtatac gaatacatta ggccttgatg gttttagaat agatgcagta aaacatataa      3900
aatacagctt tactcgtgat tggattaatc atgttagaag tgcaactggc aaaaatatgt      3960
ttgcggttgc ggaattttgg aaaaatgatt taggtgctat tgaaaactat ttaaacaaaa      4020
caaactggaa ccattcagtc tttgatgttc cgctgcacta taacctctat aatgcttcaa      4080
aaagcggagg gaattatgat atgaggcaaa tatttaatgg tacagtcgtg caaagacatc      4140
caatgcatgc tgttacattt gttgataatc atgattcgca acctgaagaa gctttagagt      4200
cttttgttga agaatggttc aaaccattag cgtatgcttt gacattaaca cgtgaacaag      4260
gctacccttc tgtattttat ggagattatt atggcattcc aacgcatggt gtaccagcga      4320
tgaaatcgaa aattgacccg attctagaag cgcgtcaaaa gtatgcatat ggaagacaaa      4380
atgactactt agaccatcat aatatcatcg gttggacacg tgaagggaat acagcacacc      4440
ccaactccgg tttagctact atcatgtccg atggggcagg aggaaataag tggatgtttg      4500
ttgggcgtaa taaagctggt caagtttgga ccgatatcac tggaaatcgt gcaggtactg      4560
ttacgattaa tgctgatgga tggggtaatt tttctgtaaa tggaggatca gtttctatt       4620
```

```
gggtaaacaa ataagtcgac ggcccagccg gccaacaggt catttttttag gagggtttac    4680
atcatggcaa tacttgttac tggcggtgcc ggttacattg gcagccacac atgtgttgaa    4740
ctattgaaca gcggctacga gattgttgtt cttgataatc tgtccaacag ttcagctgaa    4800
gcgctgaacc gtgtcaagga gattacagga aaagatttaa cgttctacga agcggattta    4860
ttggaccggg aagcggtaga ttccgttttt gctgaaaatg aaatcgaagc tgtgattcat    4920
tttgcagggt taaaagcagt cggcgaatct gtggcgattc ccctcaaata ttatcataac    4980
aatttgacag gaacgtttat tttatgcgag gccatggaga atacggcgt caagaaaatc     5040
gtattcagtt catctgcgac agtatacggc gttccgaaaa catcgccgat tacgaagac     5100
tttccattag gcgcgacaaa tccttatggg cagacgaagc tcatgcttga acaaatattg    5160
cgtgatttgc atacagccga caatgagtgg agcgttgcgc tgcttcgtta ctttaacccg    5220
ttcggcgcgc atccaagcgg acggatcggt gaagacccga acggaatccc aaataacctt    5280
atgccgtatg tggcacaggt agcagtcggg aagctcgagc aattaagcgt attcggaaat    5340
gactatccga caaaagacgg gacaggcgta cgcgattata ttcacgtcgt tgatctcgca    5400
gaaggccacg tcaaggcgct ggaaaaagta ttgaactcta caggagccga tgcatacaac    5460
cttggaacag gcacaggcta cagcgtgctg gaaatggtca agcctttga aaaagtgtca     5520
gggaaagagg ttccataccg ttttgcggac cgccgtccgg gagacatcgc cacatgcttt    5580
gcagatcctg cgaaagccaa gcgagaacta ggctgggaag cgaaacgcgg ccttgaggaa    5640
atgtgtgctg attcctggag atggcagtct tctaatgtga atgggtataa gagtgcggaa    5700
taagaatgga ggccttctca attgagaagg ccttttttaa agaacaaggg tgcctaaaca    5760
ggcacccttg ttagctgtta tttgattttc acg                                 5793
```

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4

```
ttacatccgc gggtgaggaa agacaggac                                      29
```

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5

```
tagtgaattc agaaccggtc cacatcc                                         27
```

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6

```
tgttcccgag aatggaggcc ttctcaattg                                      30
```

<210> SEQ ID NO 7
<211> LENGTH: 37

```
<212> TYPE: DNA
<213> ORGANISM: Artificial Sequence
<220> FEATURE:
<223> OTHER INFORMATION: Primer

<400> SEQUENCE: 7
tggttgtcga catctgaggg aggtacaatt gtagctg                                    37

<210> SEQ ID NO 8
<211> LENGTH: 48
<212> TYPE: DNA
<213> ORGANISM: Artificial Sequence
<220> FEATURE:
<223> OTHER INFORMATION: Primer

<400> SEQUENCE: 8
ttttcatcga tactagtgtg cacggatcca tctgaaggtc gatacggg                        48

<210> SEQ ID NO 9
<211> LENGTH: 36
<212> TYPE: DNA
<213> ORGANISM: Artificial Sequence
<220> FEATURE:
<223> OTHER INFORMATION: Primer

<400> SEQUENCE: 9
ttgtttgtcg acgcaaagct gttttatgaa ttctcc                                     36

<210> SEQ ID NO 10
<211> LENGTH: 39
<212> TYPE: DNA
<213> ORGANISM: Artificial Sequence
<220> FEATURE:
<223> OTHER INFORMATION: Primer

<400> SEQUENCE: 10
ttttggccca gccggccaac aggtcatttt ttaggaggg                                  39

<210> SEQ ID NO 11
<211> LENGTH: 39
<212> TYPE: DNA
<213> ORGANISM: Artificial Sequence
<220> FEATURE:
<223> OTHER INFORMATION: Primer

<400> SEQUENCE: 11
ttattggatc cgtgaaaatc aaataacagc taacaaggg                                  39

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
ttttcatcga taacaggtca ttttttagga ggg                                        33
```

US 6,762,040 B2

METHOD FOR INCREASING GENE COPY NUMBER IN A HOST CELL AND RESULTING HOST CELL

CROSS-REFERENCE TO RELATED APPLICATIONS

This application is a 35 U.S.C. 371 national application of PCT/DK01/00356 filed May 23, 2001 published in English under PCT Article 21(2) and claims, under 35 U.S.C. 119, priority or the benefit of Danish application no. PA 2000 00824 filed May 24, 2000 and U.S. application no. 60/208, 052 filed May 30, 2000, the contents of which are fully incorporated herein by reference.

FIELD OF THE INVENTION

The invention relates to a method for increasing the copy number of a chromosomally integrated expression cassette in a microbial strain without leaving antibiotic resistance markers behind in the strain, the necessary genetic constructs, and the strains used in and resulting from the method of the invention. It is desirable for the biotech industry to provide microbial strains devoid of antibiotic resistance markers comprising several chromosomally integrated copies of a gene of interest, for the industrial high yield production of polypeptides.

BACKGROUND OF THE INVENTION

The present debate concerning the industrial use of recombinant DNA technology has raised some questions and concern about the use of antibiotic marker genes. An antibiotic marker gene is traditionally used as a means to select for strains carrying multiple copies of both the marker gene and an accompanying expression cassette coding for a polypeptide of industrial interest. Amplification of the expression cassette by increasing the copy number in a microbiological production strain is desirable because there is very often a direct correlation between the number of copies and the final product yields. The amplification method using antibiotic selection has been used extensively in many host strains over the past 15 years and has proven to be a very efficient way to develop high yielding production strains in a relatively short time, irrespective of the expression level of the individual expression cassettes.

In order to comply with the current demand for recombinant production host strains devoid of antibiotic markers, we have looked for possible alternatives to the present technology that will allow substitution of the antibiotic markers we use today with new marker genes.

The catabolic pathway of galactose in bacilli is very similar to the pathway of other sugars. The carbon molecule is transported into the cell via a permease, a kinase charges the molecule with a phosphate group and a transferase reaction transfers the phosphate group to a glucose molecule which is then shuttled directly into the glycolytic pathway. In the case of galactose catabolism the transferase reaction generates UDP-galactose as a sideproduct which is a very toxic compound for all living cells. This compound is normally converted to UDP-glucose by an epimerase coded for by the galE gene. The use of galE in a simple selection method for plasmid transformed cells, especially plant cells, is mentioned in WO 00/09705.

SUMMARY OF THE INVENTION

The problem to be solved by the present invention is to increase the copy number of a chromosomally integrated expression cassette in a microbial strain in a way by which a resulting host cell devoid of antibiotic markers is provided for the use in industrial production of polypeptides in high yields.

The solution is based on that the present inventors demonstrated that a nucleotide construct comprising an amplification unit as defined herein can integrate into the chromosome of a host cell and increase in number of chromosomally integrated copies without the use of classical antibiotic markers or antibiotics.

Accordingly, in a first aspect the invention relates to a method for increasing the number of copies of an amplification unit integrated into a host cell chromosome, wherein the method comprises the steps of:

a) rendering a chromosomal gene of a host cell non-functional, wherein the host cell becomes susceptible to an inhibitory compound endogenously produced by the host cell when the host cell is cultivated in a medium comprising a precursor;

b) making a nucleic acid construct comprising an amplification unit, wherein the unit comprises:
  i) an expression cassette comprising at least one copy of a gene of interest; and
  ii) an expressable copy of the chromosomal gene of step a), wherein the unit integrates into the host cell chromosome;

c) introducing the nucleic acid construct of step b) into the host cell of step a), wherein at least one copy of the amplification unit integrates into the host cell chromosome;

d) cultivating the host cell of step c) in a medium comprising the precursor, wherein a chromosomally integrated copy of the amplification unit is duplicated or multiplied on the host cell chromosome;

e) selecting a host cell comprising two or more chromosomally integrated copies of the amplification unit; and optionally f) performing one or more cycles of steps d) and e) using the host cell selected in step e) in each new cycle; wherein the number of chromosomally integrated copies of the amplification unit increases with each repeat.

Further, in a second aspect the invention relates to a method for constructing a host cell comprising at least one copy of an amplification unit integrated into the host cell chromosome, wherein the method comprises the steps of:

a) rendering a chromosomal gene of a host cell non-functional, wherein the host cell becomes susceptible to an inhibitory compound endogenously produced by the host cell when the host cell is cultivated in a medium comprising a precursor;

b) making a nucleic acid construct comprising an amplification unit, wherein the unit comprises:
  i) an expression cassette comprising at least one copy of a gene of interest; and
  ii) an expressable copy of the chromosomal gene of step a), wherein the unit integrates into the host cell chromosome;

c) introducing the nucleic acid construct of step b) into the host cell of step a) and cultivating the host cell in a medium comprising the precursor, wherein at least one copy of the amplification unit integrates into the host cell chromosome; and d) selecting a host cell comprising at least one chromosomally integrated copy of the amplification unit.

A third aspect of the invention relates to a method for increasing the number of copies of an amplification unit integrated into a host cell chromosome, wherein the method comprises the steps of:

a) providing a host cell, wherein a chromosomal gene has been rendered non-functional, whereby the host cell becomes susceptible to an inhibitory compound endogenously produced by the host cell when the host cell is cultivated in a medium comprising a precursor;

b) introducing a nucleic acid construct into the host cell of step a), the nucleic acid construct comprising an amplification unit, wherein the unit comprises:
   i) an expression cassette comprising at least one copy of a gene of interest; and
   ii) an expressable copy of the chromosomal gene of step a), wherein at least one copy of the amplification unit integrates into the host cell chromosome;

c) cultivating the host cell of step b) in a medium comprising the precursor, wherein a chromosomally integrated copy of the amplification unit is duplicated or multiplied on the host cell chromosome;

d) selecting a host cell comprising two or more chromosomally integrated copies of the amplification unit; and optionally e) performing one or more cycles of steps c) and d) using the host cell selected in step d) in each new cycle; wherein the number of chromosomally integrated copies of the amplification unit increases with each cycle.

As clear from above, genetic tools are provided for performing the method of the invention as described herein.

Accordingly in a fourth aspect the invention relates to an amplification unit comprising:

a) an expression cassette comprising at least one copy of a gene of interest; and b) an expressable copy of a conditionally essential chromosomal gene of a host cell; wherein the unit integrates into the host cell chromosome upon introduction of the nucleic acid construct into the host cell.

Further in a fifth aspect the invention relates to a nucleic acid construct comprising a unit as defined in any of the previous aspects.

The method of the invention achieves the construction of a host cell comprising at least one chromosomally integrated copy of the amplification unit as defined above, where such a host cell is highly desirable for industrial production of polypeptides in high yields.

Consequently in a sixth aspect the invention relates to a host cell wherein a chromosomal gene has been rendered non-functional leaving the host cell susceptible to an inhibitory compound endogenously produced by the host cell when cultivated in a medium comprising a precursor; and wherein the host cell comprises an amplification unit as defined in any of the previous aspects or a nucleotide construct as defined in the previous aspect.

In a final aspect the invention relates to a process for producing a polypeptide of interest, wherein the process comprises a step of cultivating a host cell as defined in the previous aspect.

BRIEF DESCRIPTION OF THE FIGURES

FIG. 1 shows a Southern blot which demonstrated hybridization to flanking fragments of the dal locus and a strong hybridization band to the expression cassette corresponding to the size of the plasmid pMOL1807 (SEQ ID NO:2) in a non-limiting example herein. Definitions In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989") DNA Cloning: A Practical Approach, Volumes I and II / D. N. Glover ed. 1985); Oligonucleotide Synthesis (M. J. Gait ed. 1984); Nucleic Acid Hybridization (B. D. Hames & S. J. Higgins eds (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984).

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

A "nucleic acid molecule" or "nucleotide sequence" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization.

A DNA "coding sequence" or an "open reading frame (ORF)" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

An expression vector is a DNA molecule, linear or circular, that comprises a segment encoding a polypeptide of interest operably linked to additional segments that provide for its transcription. Such additional segments may include promoter and terminator sequences, and optionally one or more origins of replication, one or more selectable markers, an enhancer, a polyadenylation signal, and the like. Expression vectors are generally derived from plasmid or viral DNA, or may contain elements of both.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "secretory signal sequence" is a DNA sequence that encodes a polypeptide (a "secretory peptide" that, as a component of a larger polypeptide, directs the larger polypeptide through a secretory pathway of a cell in which it is synthesized. The larger polypeptide is commonly cleaved to remove the secretory peptide during transit through the secretory pathway.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A chromosomal gene is rendered non-functional if the polypeptide that the gene encodes can no longer be expressed in a functional form. Such non-functionality of a gene can be induced by a wide variety of genetic manipulations as known in the art, some of which are described in Sambrook et al. vide supra. Partial deletions within the ORF of a gene will often render the gene non-functional, as will mutations.

The term "an expressable copy of a chromosomal gene" is used herein as meaning a copy of the ORF of a chromosomal gene, wherein the ORF can be expressed to produce a fully functional gene product. The expressable copy may not be transcribed from the native promoter of the chromosomal gene, it may instead be transcribed from a foreign or heterologous promoter, or it may indeed be promoterless and expressed only by transcriptional read-through from a gene present upstream of the 5' end of the ORF. Transcriptional read-through is intended to have the same meaning here as the generally recognized meaning in the art.

"Operably linked", when referring to DNA segments, indicates that the segments are arranged so that they function in concert for their intended purposes, e.g. transcription initiates in the promoter and proceeds through the coding segment to the terminator.

A coding sequence is "under the control" of transcriptional and translational control sequences in a cell when RNA polymerase transcribes the coding sequence into mRNA, which is then trans-RNA spliced and translated into the protein encoded by the coding sequence.

"Heterologous" DNA refers to DNA not naturally located in the cell, or in a chromosomal site of the cell. Preferably, the heterologous DNA includes a gene foreign to the cell.

As used herein the term "nucleic acid construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding a polypeptide of interest. The construct may optionally contain other nucleic acid segments.

The nucleic acid construct of the invention encoding the polypeptide of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., supra).

The nucleic acid construct of the invention encoding the polypeptide may also be prepared synthetically by established standard methods, e.g. the phosphoamidite method described by Beaucage and Caruthers, Tetrahedron Letters 22 (1981), 1859–1869, or the method described by Matthes et al., EMBO Journal 3 (1984), 801–805. According to the phosphoamidite method, oligonucleotides are synthesized, e.g. in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques. The nucleic acid construct may also be prepared by polymerase chain reaction using specific primers, for instance as described in U.S. Pat. No. 4,683,202 or Saiki et al., Science 239 (1988), 487–491.

The term nucleic acid construct may be synonymous with the term "expression cassette" when the nucleic acid construct contains the control sequences necessary for expression of a coding sequence of the present invention The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcription and translation control sequences which mediate the expression of the polypeptide. The promoter may be any nucleic acid sequence which shows transcriptional activity in the host cell of choice and may be obtained from genes encoding extracellular or intracellular polypeptides either homologous or heterologous to the host cell.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the expressed polypeptide into the cell's secretory pathway of the host cell. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. A foreign signal peptide coding region may be required where the coding sequence does not normally contain a signal peptide coding region. Alternatively, the foreign signal peptide coding region may simply replace the natural signal peptide coding region in order to obtain enhanced secretion of the [enzyme] relative to the natural signal peptide coding region normally associated with the coding sequence. The signal peptide coding region may be obtained from a glucoamylase or an amylase gene from an Aspergillus species, a lipase or proteinase gene from a Rhizomucor species, the gene for the alpha-factor from *Saccharomyces cerevisiae*, an amylase or a protease gene from a Bacillus species, or the calf prepro-chymosin gene. However, any signal peptide coding region capable of directing the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, or the *Myceliophthora thermophilum* laccase gene (WO 95/33836).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be placed in tandem with the regulatory sequence.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus subtilis* alkaline protease gene, the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus amyloliquefaciens* BAN AMYLASE GENE, the *Bacillus licheniformis* penicillinase gene (penP), the *Bacillus subtilis* xylA and xylB genes, and the prokaryotic beta-lactamase gene (Villa-Kamaroff et al., 1978, Proceedings of the National Academy of Sciences USA 75:3727–3731), as well as the tac promoter (DeBoer et al., 1983, Proceedings of the National Academy of Sciences USA 80:21–25). Further promoters are described in "Useful proteins from recombinant bacteria" in Scientific American, 1980, 242:74–94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and hybrids thereof. Particularly preferred promoters for use in filamentous fungal host cells are the TAKA amylase, NA2-tpi (a hybrid of the promoters from the genes encoding *Aspergillus niger* neutral a-amylase and *Aspergillus oryzae* triose phosphate isomerase), and glaA promoters. Further suitable promoters for use in filamentous fungus host cells are the ADH3 promoter (McKnight et al., The EMBO J. 4 (1985), 2093–2099) or the tpiA promoter.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. for fungal hosts) the TPI1 (Alber and Kawasaki, op. cit.) or ADH3 (McKnight et al., op. cit.) terminators.

Preferred terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminators for yeast host cells are described by Romanos et al., 1992, supra.

An effective signal peptide coding region for bacterial host cells is the signal peptide coding region obtained from the maltogenic amylase gene from Bacillus NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* PrsA gene. Further signal peptides are described by Simonen and Palva, 1993, Microbiological Reviews 57:109–137.

An effective signal peptide coding region for filamentous fungal host cells is the signal peptide coding region obtained from *Aspergillus oryzae* TAKA amylase gene, *Aspergillus niger* neutral amylase gene, the *Rhizomucor miehei* aspartic proteinase gene, the *Humicola lanuginosa* cellulase or lipase gene, or the *Rhizomucor miehei* lipase or protease gene, Aspergillus sp. amylase or glucoamylase, a gene encoding a *Rhizomucor miehei* lipase or protease. The signal peptide is preferably derived from a gene encoding *A. oryzae* TAKA amylase, *A. niger* neutral a-amylase, *A. niger* acid-stable amylase, or *A. niger* glucoamylase.

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

A conditionally essential gene may function as a selectable marker. Examples of bacterial conditionally essential selectable markers are the dal genes from *Bacillus subtilis* or *Bacillus licheniformis*, that are only essential when the bacterium is cultivated in the presence of D-alanine; or the genes encoding enzymes involved in the removal of UDP-galactose from the bacterial cell when the cell is grown in the presence of galactose. Non-limiting examples of such genes are those from *B. subtilis* or *B. licheniformis* encoding UTP-dependent phosphorylase (EC 2.7.7.10), UDP-glucose-dependent uridylyltransferase (EC 2.7.7.12), or UDP-galactose epimerase (EC 5.1.3.2).

Antibiotic selectable markers confer antibiotic resistance to such antibiotics as ampicillin, kanamycin, chloramphenicol, tetracycline, neomycin, hygromycin or methotrexate. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Preferred for use in an Aspergillus cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, where the selectable marker is on a separate vector.

The vectors of the present invention preferably contain an element(s) that permits stable integration of the vector, or of a smaller part of the vector, into the host cell genome or autonomous replication of the vector in the cell independent of the genome of the cell.

The vectors, or smaller parts of the vectors such as amplification units of the present invention, may be integrated into the host cell genome when introduced into a host cell. For chromosomal integration, the vector may rely on the nucleic acid sequence encoding the polypeptide or any other element of the vector for stable integration of the vector into the genome by homologous or nonhomologous recombination.

Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences.

On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences. The copy number of a vector, an expression cassette, an amplification unit, a gene or indeed any defined nucleotide sequence is the number of identical copies that are present in a host cell at any time. A gene or another defined chromosomal nucleotide sequence may be present in one, two, or more copies on the chromosome. An autonomously replicating vector may be present in one, or several hundred copies per host cell.

An amplification unit of the invention is a nucleotide sequence that can integrate into the chromosome of a host cell, whereupon it can increase in number of chromosomally integrated copies by duplication of multiplication. The unit comprises an expression cassette as defined herein comprising at least one copy of a gene of interest and an expressable copy of a chromosomal gene, as defined herein, of the host cell.

For autonomous replication, the vector may further comprise an origin of replication enabling the vector to replicate autonomously in the host cell in question. Examples of bacterial origins of replication are the origins of replication of plasmids pBR322, pUC19, pACYC177, pACYC184, pUB110, pE194, pTA1060, and pAMβ1. Examples of origin of replications for use in a yeast host cell are the 2 micron origin of replication, the combination of CEN6 and ARS4, and the combination of CEN3 and ARS1. The origin of replication may be one having a mutation which makes its functioning temperature-sensitive in the host cell (see, e.g., Ehrlich, 1978, Proceedings of the National Academy of Sciences USA 75:1433).

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a Streptomyces cell, e.g., *Streptomyces lividans* or *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell.

The transformation of a bacterial host cell may, for instance, be effected by protoplast transformation (see, e.g., Chang and Cohen, 1979, Molecular General Genetics 168:111–115), by using competent cells (see, e.g., Young and Spizizin, 1961, Journal of Bacteriology 81:823–829, or Dubnar and Davidoff-Abelson, 1971, Journal of Molecular Biology 56:209–221), by electroporation (see, e.g., Shigekawa and Dower, 1988, Biotechniques 6:742–751), or by conjugation (see, e.g., Koehler and Thorne, 1987, Journal of Bacteriology 169:5771–5278).

The host cell may be a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, e.g., Neurospora, Eupenicillium (=Penicillium), Emericella (=Aspergillus), Eurotium (=Aspergillus), and the true yeasts listed above. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., Saprolegniomycetous aquatic fungi (water molds) such as Achlya. Examples of mitosporic fungi include Aspergillus, Penicillium, Candida, and Alternaria. Representative groups of Zygomycota include, e.g., Rhizopus and Mucor.

The fungal host cell may be a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus Schizosaccharomyces), Nadsonioideae, Lipomycoideae, and Saccharomycoideae (e.g., genera Pichia, Kluyveromyces and Saccharomyces). The basidiosporogenous yeasts include the genera Leucosporidim, Rhodosporidium, Sporidiobolus, Filobasidium, and Filobasidiella. Yeast belonging to the Fungi Imperfecti are divided into two families, Sporobolomycetaceae (e.g., genera Sorobolomyces and Bullera) and Cryptococcaceae (e.g., genus Candida). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., Biochemistry and Genetics of Yeast, Bacil, M., Horecker, B. J., and Stopani, A. O. M., editors, 2nd edition, 1987; The Yeasts, Rose, A. H., and Harrison, J. S., editors, 2nd edition, 1987; and The Molecular Biology of the Yeast Saccharomyces, Strathern et al., editors, 1981). The yeast host cell may be selected from a cell of a species of Candida, Kluyveromyces, Saccharomyces, Schizosaccharomyces, Candida, Pichia, Hansenula, or Yarrowia. In a preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. Other useful yeast host cells are a *Kluyveromyces lactis, Kluyveromyces fragilis, Hansenula polymorpha, Pichia pastoris, Yarrowia lipolytica, Schizosaccharomyces pombe, Ustilgo maylis, Candida maltose, Pichia guillermondii* and *Pichia methanolio* cell (cf. Gleeson et al., J. Gen. Microbiol. 132, 1986, pp. 3459–3465; U.S. Pat. No. 4,882,279 and U.S. Pat. No. 4,879,231).

The fungal host cell may be a filamentous fungal cell. "Filamentous fungi" include all filamentous forms of the subdivision Eumycota and Oomycota (as defined by Hawksworth et al., 1995, supra). The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, and Trichoderma or a teleomorph or synonym thereof. In an even more preferred embodiment, the filamentous fungal host cell is an Aspergillus cell. In another even more preferred embodiment, the filamentous fungal host cell is an Acremonium cell. In another even more preferred embodiment, the filamentous fungal host cell is a Fusarium cell. In another even more preferred embodiment, the filamentous fungal host cell is a Humicola cell. In another even more preferred embodiment, the filamentous fungal host cell is a Mucor cell. In another even more preferred embodiment, the filamentous fungal host cell is a Myceliophthora cell. In another even more preferred embodiment, the filamentous fungal host cell is a Neurospora cell. In another even more preferred embodiment, the filamentous fungal host cell is a Penicillium cell. In another even more preferred embodiment, the filamentous fungal host cell is a Thielavia cell. In another even more preferred embodiment, the filamentous fungal host cell is a Tolypocladium cell. In another even more preferred embodiment, the filamentous fungal host cell is a Trichoderma cell. In a most preferred embodiment, the filamentous fungal host cell is an *Aspergillus awamori, Aspergillus foetidus, Aspergillus japonicus, Aspergillus niger, Aspergillus nidulans* or *Aspergillus oryzae* cell. In another most preferred embodiment, the filamentous fungal host cell is a Fusarium cell of the section Discolor (also known as the section Fusarium). For example, the filamentous fungal parent cell may be a *Fusarium bactridioides, Fusarium cerealis, Fusarium crookwellense, Fusarium culmorum, Fusarium graminearum, Fusarium graminum, Fusarium heterosporum, Fusarium negundi, Fusarium reticulatum, Fusarium roseum, Fusarium sambucinum, Fusarium sarcochroum, Fusarium sulphureum,* or *Fusarium trichothecioides* cell. In another preferred embodiment, the filamentous fungal parent cell is a Fusarium strain of the section Elegans, e.g., *Fusarium oxysporum*. In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a Myceliophthora thermophilum cell. In another most preferred embodiment, the filamentous fungal host cell is a Neurospora crassa cell. In another most preferred embodiment, the filamentous fungal host cell is a *Penicillium purpurogenum* cell. In another most preferred embodiment, the filamentous fungal host cell is a Thielavia terrestris cell or an *Acremonium chrysogenum* cell. In another most preferred embodiment, the Trichoderma cell is a *Trichoderma harzianum, Trichoderma koningii, Trichoderma longibrachiatum, Trichoderma reesei* or *Trichoderma viride* cell.

The use of Aspergillus spp. for the expression of proteins is described in, e.g., EP 272 277, EP 230 023. Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, Proceedings of the National Academy of Sciences USA 81:1470–1474. A suitable method of transforming Fusarium species is described by Malardier et al., 1989, Gene 78:147–156 or in copending U.S. Pat. No. Ser. No. 08/269,449. Examples of other fungal cells are cells of filamentous fungi, e.g. Aspergillus spp., Neurospora spp., Fusarium spp. or Trichoderma spp., in particular strains of *A. oryzae, A. nidulans* or *A. niger*. The transformation of *F. oxysporum* may, for instance, be carried out as described by Malardier et al., 1989, Gene 78: 147–156.

Yeast may be transformed using the procedures described by Becker and Guarente, In Abelson, J. N. and Simon, M. I., editors, Guide to Yeast Genetics and Molecular Biology, Methods in Enzymology, Volume 194, pp 182–187, Academic Press, Inc., New York; Ito et al., 1983, Journal of Bacteriology 153:163; and Hinnen et al., 1978, Proceedings of the National Academy of Sciences USA 75:1920. Mammalian cells may be transformed by direct uptake using the calcium phosphate precipitation method of Graham and Van der Eb (1978, Virology 52:546).

The transformed or transfected host cells described above are cultured in a suitable nutrient medium under conditions permitting the expression of the desired polypeptide, after which the resulting polypeptide is recovered from the cells, or the culture broth.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media are prepared using procedures known in the art (see, e.g., references for bacteria and yeast; Bennett, J. W. and LaSure, L., editors, More Gene Manipulations in Fungi, Academic Press, CA, 1991).

If the polypeptide is secreted into the nutrient medium, the polypeptide can be recovered directly from the medium. If the polypeptide is not secreted, it is recovered from cell lysates. The polypeptide are recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989).

DETAILED DESCRIPTION OF THE INVENTION

A method for increasing the number of copies of an amplification unit integrated into a host cell chromosome, according to the first, second, or/third aspect of the invention.

In the industry there are a number of preferred bacterial host cells, especially Gram-positive microorganisms are desirable.

Accordingly in a preferred embodiment the invention relates to the method of the first two aspects, wherein the host cell is a Gram-positive bacterial cell, preferably a Bacillus cell, more preferably a Bacillus cell of a species chosen from the group consisting of *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; and most preferably a *Bacillus licheniformis* cell.

A host cell is susceptible to an inhibitory compound, if the host cell has reduced growth rate in the presence of the compound when compared to the growth rate in the absence of the compound in a growth medium, or if the host cell becomes non-culturable in the presence or the compound, or if the host cell is killed in the presence of the compound. Antibiotics fall under this definition of inhibitory compounds however not all inhibitory compounds are classified as classical antibiotics.

The inhibitory compound may be endogenously produced by the host cell as part of the host cell's normal metabolism, where the compound is normally not found in inhibitory concentrations. Rendering a chromosomal gene of the host cell non-functional may result in the accumulation of an endogenously produced inhibitory compound within the host cell resulting in an inhibitory concentration of the compound. In some cases the inhibitory compound is only produced in the host cell when the host cell is cultivated in the presence of a precursor. In a preferred embodiment of the invention the inhibitory compound is UDP-galactose.

Preferable examples of precursors are galactose containing compounds—such as lactoses, melibioses, raffinoses, stachyoses, verbascoses and galactinola. More preferable precursors of galactose include alpha-lactose (beta-D-galactopyranosyl-[1→4]-alpha-D-glucose), and other substrates which liberates free D-galactose upon hydrolysis by either alpha-galactosidases or beta-galactosidases. Other examples of potentially useful precursors for use in the method of the invention are chemically derivatized forms of galactose, preferably chemical derivatives of D-galactose, from which D-galactose can be liberated by use of appropriate techniques, such as enzyme action, where the appropriate enzyme may be comprised in the medium or may be added to the medium or may indeed be secreted into the medium by the host cell. By way of example suitable derivatives are D-galactose pentaacetate and D-galactose methyl galactoside. Preferably the medium may comprise a derivative of galactose, such as galactose-1-phosphate or UDP-galactose.

Accordingly in a preferred embodiment the invention relates to the method of the first, second or third aspects, wherein the chromosomal gene of step a) encodes an enzyme, preferably chosen from the group consisting of galactokinase (EC 2.7.1.6), UTP-dependent pyrophosphorylase (EC 2.7.7.10), UDP-glucose-dependent uridylyltransferase (EC 2.7.7.12), UDP-galactose epimerase (EC 5.1.2.3); more preferably the chromosomal gene of step a) encodes an enzyme with UDP-galactose epimerase activity (EC 5.1.2.3), and most preferably the chromosomal gene of step a) is galE.

Further in a preferred embodiment the invention relates to the method of the first, second, or third aspects, wherein the inhibitory compound is UDP-galactose.

Still further in a preferred embodiment the invention relates to the method of the first, second, or third aspects, wherein the precursor is free galactose, preferably free D-galactose; more preferably the precursor can be degraded to produce free galactose, or preferably free D-galactose; even more preferably the precursor is lactose, melibiose, raffinose, stachyose, verbascose or galactinol.

Another preferred embodiment of the invention relates to the method of the first, second, or third aspects, wherein the medium comprises an enzyme capable of degrading the precursor to produce free galactose, or preferably free D-galactose.

One preferred embodiment of the invention relates to the method of the first, second, or third aspects, wherein the host cell secretes an enzyme into the medium which is capable of degrading the precursor to produce free galactose, or preferably free D-galactose, preferably the enzyme is a galactosidase, preferably an alpha-galactosidase or a beta-galactosidase.

As mentioned above this invention also concerns a nucleic acid construct as defined elsewhere herein along with one or more components also described elsewhere herein that may be comprised in the construct.

Consequently a preferred embodiment of the invention relates to the method of the first, second, or third aspects, wherein the nucleic acid construct is a plasmid.

In a non-limiting example shown herein of the method of the invention it is demonstrated how antibiotic selectable markers may be comprised in the nucleic acid construct of the invention, and also how such markers may eventually be removed from the host cell by the help of specific resolvase enzymes, a technique which is well known in the art.

Accordingly a preferred embodiment of the invention relates to the method of the first, second, or third aspects, wherein the nucleic acid construct further comprises an antibiotic selection marker, preferably flanked by resolvase sites or res-sites.

As described supra chromosomal integration of a vector or a smaller part of a vector—such as an amplification unit as defined supra—into the genome of the host cell can be achieved by a number of ways. A non-limiting example of integration by homologous recombination was shown herein.

A preferred embodiment of the invention relates to the method of the first, second, or third aspects, wherein the amplification unit further comprises a nucleotide sequence with a homology to a chromosomal nucleotide sequence of the host cell sufficient to effect chromosomal integration in the host cell of the amplification unit by homologous recombination, preferably the amplification unit further comprises a nucleotide sequence of at least 100 bp, preferably 200 bp, more preferably 300 bp, even more preferably 400 bp, and most preferably at least 500 bp with an identity of at least 70%, preferably 80%, more preferably 90%, even more preferably 95%, and most preferably at least 98% identity to a chromosomal nucleotide sequence of the host cell.

In a non-limiting example integration into the chromosome of a host cell can be selected for by first rendering a conditionally essential host cell gene non-functional as described elsewhere herein, thereby rendering the host cell selectable, then targetting the vector's integration by including on this a likewise non-functional copy of same host gene of a size that allows homologous recombination between the two different copies of the non-functional host genes in the genome of the host cell and on the integration vector—where such a recombination will restore a functional copy of the gene, thus leaving the host cell selectable.

Accordingly a preferred embodiment of the invention relates to the method of the first, second, or third aspects, wherein the nucleotide sequence comprised in the amplification unit is a partial non-functional copy of a conditionally essential gene of the host cell, wherein the host cell prior to the first step of the invention has had the conditionally essential gene rendered non functional by a partial deletion, and wherein a recombination event between the partial copy of the gene comprised in the amplification unit and the partial chromosomal gene restores a functional chromosomal gene; preferably the conditionally essential gene encodes a D-alanine racemase, preferably the conditionally essential gene is dal.

Another preferred embodiment of the invention relates to the method of the first, second, or third aspects, wherein a first amplification unit integrates into the host cell chromosome by homologous recombination with the partially deleted conditionally essential gene and renders the gene functional.

Yet another preferred embodiment of the invention relates to the method of the first, second, or third aspects, wherein the amplification unit further comprises an antibiotic marker, preferably flanked by resolvase sites or res-sites; preferably a host cell comprising a first chromosomally integrated amplification unit is selected and the antibiotic marker excised from the host cell chromosome by a resolvase prior to the next step in the method.

In the industrial production of polypeptides it is of interest to cultivate a host cell comprising several copies of a gene encoding a polypeptide of interest to achieve high yields.

A preferred embodiment of the invention relates to the method of the first, second, or third aspects, wherein the gene of interest encodes a polypeptide of interest, preferably the polypeptide is an enzyme such as a protease; a cellulase; a lipase; a xylanase; a phospholipase; or preferably an amylase.

Another preferred embodiment of the invention relates to the method of the first, second, or third aspects, wherein the polypeptide is a hormone, a pro-hormone, a pre-pro-hormone, a small peptide, a receptor, or a neuropeptide.

In the present invention the expressably copy of a chromosomal gene as defined above is transcribed at a reduced level compared to the wild type level of the gene in the host cell.

One preferred embodiment of the invention relates to the method of the first, second, or third aspects, wherein the expressable copy of the chromosomal gene comprised in an amplification unit integrated in the host cell chromosome has a reduced transcription level compared to the transcription level of the wild type gene of the host cell, preferably the transcription level is reduced with a factor of 100, preferably 50, more preferably 10, even more preferably 5, and most preferably with a factor of 2; preferably the expressable copy of the chromosomal gene comprised in the amplification unit is promoterless, more preferably the expressable copy of the chromosomal gene comprised in the amplification unit has a transcription terminator located upstream of the gene.

In a non-limiting example herein the gene of interest is located upstream from the expressable copy of the chromosomal gene and the two genes are co-transcribed from the promoter of the gene of interest.

A preferred embodiment of the invention relates to the method of the first, second, or third aspects, wherein the gene of interest is located upstream of the expressable copy of the chromosomal gene within the amplification unit and wherein the two genes are co-directionally transcribed; preferably the expressable copy of the chromosomal gene is expressed by read-through transcription from the gene of interest.

The method of the present invention provides a number of genetic tools that are advantageous in the invention.

In a preferred embodiment the invention relates to the amplification unit of the fourth aspect of the invention wherein the chromosomal gene encodes an enzyme, preferably chosen from the group consisting of galactokinase (EC 2.7.1.6), UTP-dependent pyrophosphorylase (EC 2.7.7.10), UDP-glucose-dependent uridylyltransferase (EC 2.7.7.12), UDP-galactose epimerase (EC 5.1.2.3); preferably the chromosomal gene encodes an enzyme with UDP-galactose epimerase activity (EC 5.1.2.3); more preferably the chromosomal gene is galE.

In the industrial production of polypeptides it is of interest to cultivate a host cell comprising several copies of a gene encoding a polypeptide of interest to achieve high yields.

Accordingly a preferred embodiment of the invention relates to the amplification unit of the fourth aspect of the invention wherein the gene of interest encodes a polypeptide of interest; preferably the polypeptide is an enzyme such as a protease; a cellulase; a lipase; a xylanase; a phospholipase; or preferably an amylase.

Another preferred embodiment of the invention relates to the amplification unit of the fourth aspect of the invention wherein the polypeptide is a hormone, a pro-hormone, a pre-pro-hormone, a small peptide, a receptor, or a neuropeptide.

Yet another preferred embodiment of the invention relates to the amplification unit of the fourth aspect of the invention wherein the expressable copy of the chromosomal gene is promoterless; preferably the expressable copy of the chromosomal gene has a transcription terminator located upstream of the gene; and preferably the gene of interest is located upstream of the expressable copy of the chromosomal gene and wherein the two genes are codirectionally transcribed, more preferably the expressable copy of the chromosomal gene is expressed by read-through transcription from the gene of interest.

A preferred embodiment of the invention relates to the amplification unit of the fourth aspect of the invention which further comprises an antibiotic marker, preferably flanked by resolvase sites or res-sites.

As mentioned above the method of invention also provides a number of genetic tools, a nucleic acid construct comprising a unit as defined in any of the previous embodiments of the fourth aspect.

The method of the invention provides a host cell of interest for the industry; a host cell wherein a chromosomal gene has been rendered non-functional leaving the host cell susceptible to an inhibitory compound endogenously produced by the host cell when cultivated in a medium comprising a precursor; and wherein the host cell comprises an amplification unit as defined in any of the embodiments of the fourth aspect or a nucleotide construct as defined in the fifth aspect.

Accordingly a preferred embodiment of the invention relates to the host cell of the sixth aspect, wherein the host cell is a Gram-positive bacterial cell, preferably a Bacillus cell, more preferably a Bacillus cell of a species chosen from the group consisting of *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; and most preferably a *Bacillus licheniformis* cell.

In another preferred embodiment the invention relates to the host cell of the sixth aspect, wherein the chromosomal gene encodes an enzyme, preferably the enzyme is chosen from the group of enzymes consisting of galactokinase (EC 2.7.1.6), UTP-dependent pyrophosphorylase (EC 2.7.7.10), UDP-glucose-dependent uridylyltransferase (EC 2.7.7.12), UDP-galactose epimerase (EC 5.1.2.3), more preferably the enzyme is an UDP-galactose epimerase (EC 5.1.2.3), and most preferably the enzyme is encoded by galE.

In yet another preferred embodiment the invention relates to the host cell of the sixth aspect, where the inhibitory compound is UDP-galactose and preferably where the precursor is free galactose, preferably free D-galactose; even more preferably the precursor can be degraded to produce free galactose, or preferably free D-galactose; even more preferably the precursor is lactose, melibiose, raffinose, stachyose, verbascose or galactinol; yet even more preferably the medium comprises an enzyme capable of degrading the precursor to produce free galactose, or preferably free D-galactose.

A preferred embodiment of the invention relates to the host cell of the sixth aspect, where the host cell secretes an enzyme into the medium which is capable of degrading the precursor to produce free galactose, or preferably free D-galactose; more preferably the enzyme is a galactosidase, preferably an alpha-galactosidase or a beta-galactosidase.

Another preferred embodiment of the invention relates to the host cell of the sixth aspect, wherein the amplification unit further comprises a nucleotide sequence of at least 100 bp, preferably 200 bp, more preferably 300 bp, even more preferably 400 bp, and most preferably at least 500 bp with an identity of at least 70%, preferably 80%, more preferably 90%, even more preferably 95%, and most preferably at least 98% identity to a chromosomal nucleotide sequence of the host cell.

A preferred embodiment of the invention relates to the host cell of the sixth aspect, wherein the nucleotide sequence comprised in the amplification unit is a partial nonfunctional copy of a conditionally essential gene of the host cell, wherein the host cell has had the conditionally essential gene rendered non functional by a partial deletion, and wherein a recombination event between the partial copy of the gene comprised in the amplification unit and the partial chromosomal gene has restored a functional chromosomal gene; preferably the conditionally essential gene encodes a D-alanine racemase, preferably the conditionally essential gene is dal.

Another preferred embodiment of the invention relates to the host cell of the sixth aspect, wherein the expressable copy of the chromosomal gene of the amplification unit has a reduced transcription level compared to the transcription level of the wild type gene of the host cell, preferably the transcription level is reduced with a factor of 100, preferably 50, more h preferably 10, even more preferably 5, and most preferably with a factor of 2.

Finally the invention provides a process for producing a polypeptide of interest, wherein the process comprises a step of cultivating a host cell as defined in any of the embodiments of the sixth aspect.

Accordingly a preferred embodiment of the invention relates to the process of the final aspect, wherein the polypeptide is an enzyme such as a protease; a cellulase; a lipase; a xylanase; a phospholipase; or preferably an amylase.

Another preferred embodiment of the invention relates to the process of the final aspect, wherein the polypeptide is a hormone, a pro-hormone, a pre-pro-hormone, a small peptide, a receptor, or a neuropeptide.

Introduction to Examples

In order to use the galE gene as a marker in *B. subtilis*, it is necessary to delete the native galE gene on the chromosome. This mutant will be tested on different medias with and without galactose and glucose to confirm the phenotype.

To enable an evaluation of the galE gene as an amplification marker, we decided to subclone the gene on an amplification vector comprising an AA560 amylase encoding gene as a reporter enzyme to determine the actual expression level of clones with single and multiple copies. Selection for multiple copies of the galE gene requires that the gene is expressed at a very low level. A weakly expressed galE gene will assure that only clones with many copies and sufficient expression of the epimerase will allow growth in the presence of galactose. The subduing of galE expression is done by subcloning galE without expression signals downstream of the transcriptional terminator of the AA560 amylase gene. Transcription of galE is then dependant of the AA560 promoter and the very limited transcriptional read-through of the terminator.

The amplification vector also comprises the C-terminal part of the dal gene which can complement a dal-minus *B. subtilis* with a C-terminal deletion of the dal gene. Transformation of the dal-minus *B. subtilis* with this amplification plasmid will enable direct selection for integration at the dal locus, when plated on media without D-alanine.

Materials and Methods

Strains and Donor Organisms

*Bacillus subtilis* PL1801: This strain is a *B. subtilis* DN1885 which has disrupted apr and npr genes (Diderichsen, B et al. 1990. Cloning of aldB, which encodes alpha-acetolactate decarboxylase, an exoenzyme from Bacillus brevis. J. Bacteriol., 172, 4315–4321).

*B. subtilis* DN1886: This strain is a *B. subtilis* DN1885 with a disrupted dal gene.

*B. subtilis* PL1955: This strain is a *B. subtilis* PL1801 carrying the plasmid pE194 which can deliver the RepF protein to support replication of replication-minus pE194 derivatives lacking the repF gene.

*B. subtilis* MOL1794: This strain is a *B. subtilis* PL1801 where the galE gene was replaced with a kanamycine resistance gene by use of the plasmid pMOL1748 (SEQ ID NO:1).

*B. subtilis* MOL1805: This strain is a DN1686 (dal-) strain where the galE gene was replaced with a kanamycine resistance gene.

*B. subtilis* MOL1875: This strain is a MOL1805 where the kanamycine resistance gene gene was excised (dal-, galE-, no antibiotic markers).

Plasmids pMOL1748 (SEQ ID NO:1): This plasmid is a pE194 derivative (Horinouchi, S and Weisblum, B., 1982, J. Bacteriol. 150:804–814) essentially containing elements making the plasmid propagatable in *Bacillus subtilis*, a kanamycin resistance gene, a gene conferring resistance to erythromycine, two flanking fragments from *B. subtilis* galE inserted upstream and downstream of the kanamycine resistance gene, two direct repeats that signify the res site from pAMβ1 and a fragment from pUB110 coding for the origin of transfer (McKenzie, T. et al., 1986, Plasmid 15:93–103). This plasmid is used for deleting the galE gene in the *B. subtilis* strains PL1801 and DN1686.

TABLE 1 pMOL1748 (6405 bp)

| Position (bp) | Size (bp) | Element (bp) | Origin |
|---|---|---|---|
| 429–432 | 4 | Linker | Synthetic |
| 433–605 | 173 | res site from pAMβ1 | E. faecalis |
| 606–978 | 373 | Downstream galE seq | B. subtilis |
| 979–1038 | 60 | Linker | Synthetic |
| 1039–4768 | 3730 | pE194 | S. aureus |
| 4769–4779 | 11 | Linker sequence | Synthetic |
| 4780–5317 | 538 | PUB110 | S. aureus |
| 5318–5342 | 25 | Linker | Synthetic |
| 5343–5666 | 324 | Upstream galE seq. | B. subtilis |
| 5667–5685 | 19 | Linker | Synthetic |
| 5686–5858 | 173 | Res site from pAMβ1 | E. faecalis |
| 5859–5864 | 6 | Linker | Synthetic |
| 5865–428 | 969 | PUB110 (Kan gene) | S. aureus | pMOL1807 (SEQ ID NO:2) and pMOL1809 (SEQ ID NO:3): These plasmids are replication-minus pE194 derivatives (Horinouchi, S and Weisblum, B., 1982, J. Bacteriol. 150:804–814) containing the origin of replication but lacking the repF gene coding for the replication protein. The repF deleted plasmid is totally dependant on replication protein delivered in trans from either a second plasmid or a chromosomally encoded repF gene in order to replicate. The plasmids codes for the kanamycine resistance gene, an alpha-amylase designated AA560, a promoterless galE gene of B. subtilis, the C-terminal part of a dal gene for complementation of the dal-minus phenotype in DN1686 and derivatives thereof (such as MOL1875). The alpha-amylase gene and the galE gene are transcriptionally fused in both plasmids but the pMOL1807 (SEQ ID NO:2) plasmid also has a transcriptional terminator located between the two genes, which only allows minor transcriptional readthrough. These plasmids are used for integration and amplification studies in the dal locus of MOL1875.

TABLE 2 pMOL1807 (5943 bp)

| Position (bp) | Size (bp) | Element (bp) | Origin |
|---|---|---|---|
| 5–828 | 824 | C-terminal dal sequence | B. subtilis |
| 829–833 | 5 | Linker sequence | Synthetic |
| 834–2045 | 1212 | pUB110 (Kana) | S. aureus |
| 2046–2066 | 21 | Linker sequence | Synthetic |
| 2067–2316 | 250 | pE194 (ori) | S. aureus |
| 2317–2328 | 12 | Linker sequence | Synthetic |
| 2329–2884 | 556 | pUB110 (oriT) | S. aureus |
| 2885–2904 | 20 | Linker sequence | Synthetic |
| 2905–3167 | 263 | amyL promoter and signal peptide | B. licheniformis |
| 3168–3176 | 9 | Linker sequence | Synthetic |
| 3177–4631 | 1455 | Alpha-amylase AA560 (NN5820) | B. species |
| 4632–4660 | 29 | Linker sequence | Synthetic |
| 4661–4776 | 116 | AmyL terminator | B. licheniformis |
| 4777–4803 | 27 | Linker sequence | Synthetic |
| 4804–5942 | 1139 | GalE | B. subtilis |
| 5943–4 | 5 | Linker sequence | Synthetic |

TABLE 3 pMOL1809 (5793 bp)

| Position (bp) | Size (bp) | Element (bp) | Origin |
|---|---|---|---|
| 5–828 | 824 | C-terminal dal sequence | B. subtilis |
| 829–833 | 5 | Linker sequence | Synthetic |
| 834–2045 | 1212 | pUB110 (Kana) | S. aureus |
| 2046–2066 | 21 | Linker sequence | Synthetic |
| 2067–2316 | 250 | pE194 (ori) | S. aureus |
| 2317–2328 | 12 | Linker sequence | Synthetic |
| 2329–2884 | 556 | pUB110 (oriT) | S. aureus |
| 2885–2904 | 20 | Linker sequence | Synthetic |
| 2905–3167 | 263 | amyL promoter and signal peptide | B. licheniformis |
| 3168–3176 | 9 | Linker sequence | Synthetic |
| 3177–4631 | 1455 | Alpha-amylase AA560 (NN5820) | B. species |
| 4632–4653 | 22 | Linker sequence | Synthetic |
| 4654–5792 | 1139 | AmyL terminator | B. licheniformis |
| 5793–4 | 5 | Linker sequence | Synthetic | pWT: a temperature sensitive, high copy number pAM 1 derivative plasmid comprising a gene coding for the resolvase enzyme from pAMbeta1 which can act on resolvase recognition sites (res) and an Erm resistance marker.

Media

TY (as described in Ausubel, F. M. et al. (eds.) "Current protocols in Molecular Biology". John Wiley and Sons, 1995).

LB agar (as described in Ausubel, F. M. et al. (eds.) "Current protocols in Molecular Biology". John Wiley and Sons, 1995). LBP is LB agar supplemented with 0.05 M potassium phosphate, pH 7.0. LBPG is LB agar supplemented with 0.5% Glucose and 0.05 M potassium phosphate, pH 7.0. LBPSK is LB agar supplemented with 0.05 M potassium phosphate, pH 7.0 and 1% of skimmed milk.

BPX media is described in EP 0 506 780 (WO 91/09129).

TSS agar (as described in Fouet A. and Sonenshein, A. L. (1990) A Target for Carbon Source-Dependant Negative Regulation of the citB Promoter of Bacillus subtilis. J. Bacteriol., 172, 835–844).

TSSara medium is TSS medium supplemented with 0.2% arabinose

When appropriate, glucose was replaced with 0.5% galactose unless otherwise stated. For plates, 2% agar was added for solid media. For amylase phenotypic detection the plates were supplemented with 0.2% starch. When appropriate 10 mg/ml kanamycine was added.

Propagation of PL1801 strain.

The Bacillus subtilis strain PL1801 was propagated in liquid medium 3 as specified by ATCC (American Type Culture Collection, USA). After 18 hours incubation at 37° C. and 300 rpm, the cells were harvested, and genomic DNA was isolated by the method described below.

Genomic DNA Preparation

The Bacillus subtilis strain PL1801 was propagated in liquid media as described above. The cells were harvested, and genomic DNA was isolated by the method described by Pitcher et al. 1989. Rapid extraction of bacterial genomic DNA with guanidium thiocyanate; Lett Appl Microbiol 8:151–156.

General Molecular Biology Methods

Unless otherwise mentioned the DNA manipulations and transformations were performed using standard methods of molecular biology (Sambrook et al. 1989. Molecular cloning: A laboratory manual, Cold Spring Harbor lab., Cold Spring Harbor, NY; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Competent cells were prepared and transformed as described by Yasbin, R. E. et al. 1975. Transformation and transfection in lysogenic strains of Bacillus subtilis: evidence for selective induction of prophage in competent cells. J. Bacteriol, 121:296–304.

Enzymes for DNA manipulations were used according to the specifications of the suppliers (e.g. restriction endonucleases, ligases etc. are obtainable from New England Biolabs, Inc.).

PCR reactions were performed using High Fidelity DNA Polymerase (Boeringer Mannheim) according to manufacturers instructions. The PCR reaction was set up in PCR buffer containing 200 $\mu$M of each dNTP, 2.5 units of High Fidelity DNA Polymerase and 100 pmol of each primer.

The PCR reactions were performed using a DNA thermal cycler PTC-200 (MJ Research). One incubation at 94° C. for 1 min followed by thirty cycles of PCR performed using a cycle profile of denaturation at 94° C. for 10 sec, annealing at 60° C. for 30 sec, and extension at 72° C. for 2 min. Five $\mu$l aliquots of the amplification product were analysed by electrophoresis in 0.7% agarose gels (NuSieve, FMC) to verify a DNA fragment of the correct size.

Fermentations

Fermentations to evaluate amylase yields were performed in shake flasks with 100 ml BPX at 300° C., 300 rpm for five days. Culture volumes of 10 ml were harvested and centrifuged at 10.000 g to remove cells and debris. The clear supernatants were used for assaying alpha-amylase activity or were loaded on SDS gels.

Assay for Alpha-amylase Activity

Alpha-amylase activity was determined by a method employing an enzymatic colorimetric test with 4,6-ethylidene(G7)-p-nitrophenyl(G1)-a,D-maltoheptaoside (ethylidene-G7PNP) as substrate (Boehringer Mannheim, Germany art. 1442309). Under a specified set of conditions (temp., pH, reaction time, buffer conditions) 1 mg of a given alpha-amylase will hydrolyse a certain amount of substrate and a yellow colour will be produced. The colour intensity is measured at 405 nm. The measured absorbance is directly proportional to the activity of the alpha-amylase in question under the given set of conditions.

SDS-page

SDS-page was performed on a Novex (Novex, San Diego) gradient Tricine 10–20% gel under denaturing conditions as prescribed by manufacturer.

EXAMPLES

Deletion of galE in B. subtilis

A temperature sensitive plasmid was constructed for the purpose of deleting the galE gene in B. subtilis. Two flanking sequences upstream and downstream of the galE gene were amplified by PCR and inserted on each side of a kanamycine (Kan) marker in the plasmid which further comprised an erythromycine (Erm) resistance marker. The primer sequences used in the PCR amplifications are as follows:

```
Upstream galE fragment:
B5860H10 (SEQ ID NO:4): TTACATCCGCGGGTGAGGAAAGACAGGAC
B5860H11 (SEQ ID NO:5): TAGTGAATTCAGAACCGGTCCACATCC Downstream galE fragment:
181804 (SEQ ID NO:6): TGTTCCCGAGAATGGAGGCCTTCTCAATTG
181805 (SEQ ID NO:7): TGGTTGTCGACATCTGAGGGAGGTACAATTGTAGCTG
```

The resulting plasmid pMOL1748 (SEQ ID NO:1) was transferred to B. subtilis PL1801 and plated on LBPG media with 5 $\mu$g/ml erytromycine (Erm). The colonies were re-streaked twice on plates at 500° C. to select for integration of the plasmid at the galE locus. The clones were grown in plain TY at 330C over 4 days to allow for excition and loss of the plasmid leaving the Kan marker in place of the galE gene. The strain MOL1794 was screened as being Kan resistant and Erm sensitive.

A galE deletion strain designated MOL1794 was tested on selective TSS minimal media supplemented with 0.2% galactose and 0.2% gluconate. The original B. subtilis PL1801 (galE+) strain showed fine growth on these plates while the galE− strain MOL 1794 showed no growth even after several days of incubation. On control TSS plates supplemented with 0.2% gluconate, both strains grew. The reported toxic effect of galactose on a galE− strain is therefore confirmed.

The galE deletion was transferred to an isogenic D-alanine racemase negative (dal−) strain designated DN 1886 by simple chromosomal transformation and selection for transfer of the Kan resistance. A dal− galE− strain was isolated and designated MOL1805.

The Kan resistance marker located in the galE locus of MOL1794 and MOL1805 was flanked by resolvase recognition sites (res) which allow a specific excision reaction in the presence of a resolvase. In order to remove the Kan marker from the chromosome, MOL1794 and MOL1805 were both transformed with pWT which is a temperature sensitive plasmid comprising a gene coding for resolvase and an Erm resistance marker. Transformants were selected on plates with 5 $\mu$g/ml Erm, they were tested for loss of the Kan marker and further re-streaked twice on plates with no antibiotics at 500° C. to cure the strains of the pWT plasmid. Selected clones were screened for loss of Erm resistance and Kan resistance and were designated MOL1875 (DN1886, dal−, galE−; no antibiotic markers) and MOL1877 (PL1801, galE−; no antibiotic markers).

Amplification Plasmids

Two different amplification plasmids with (pMOL1807; SEQ ID NO:2) and without (pMOL1809; SEQ ID NO:3) a transcriptional terminator between the AA560 amylase encoding gene and galE were constructed. The PCR-primers used for fragment amplification in the construction of the plasmids were as follows:

```
C-terminal dal fragment:
188502 (SEQ ID NO:8):  TTTTCATCGATACTAGTGTGCACGGATCCATCTGAAGGTCGATACGGG
188836 (SEQ ID NO:9):  TTGTTTGTCGACGCAAAGCTGTTTTATGAATTCTCC galE fragment primers:
190694 (SEQ ID NO:10): TTTTGGCCCAGCCGGCCAACAGGTCATTTTTTAGGAGGG
190695 (SEQ ID NO:11): TTATTGGATCCGTGAAAATCAAATAACAGCTAACAAGGG
190697 (SEQ ID NO:12): TTTTCATCGATAACAGGTCATTTTTTAGGAGGG
```

Amplification Experiments

The two amplification plasmids pMOL1807 (SEQ ID NO:2) and pMOL1809 (SEQ ID NO:3) were introduced by transformation into MOL1875 (dal−, galE−) and plated on solid LBPA media (LB+phosphate+0.2% starch) without D-alanine to select for complementation of the dal phenotype. Transformants growing on these plates had integrated the plasmids into the dal locus and converted the dal− phenotype to dal+. All transformants showed clearing zones on the starch medium plates which indicated integration and expression of the AA560 amylase also. The site of integration was verified by PCR and the clones were re-streaked on TSSara minimal media both with and without galactose to study the galE expression. Clones with integration of pMOL1807 (SEQ ID NO:2) holding the terminator between the AA560 amylase and the galE gene showed no growth on galactose plates. This phenotype demonstrated that a single copy of the artificial AA560-galE fusion in this construct did not express sufficient GalE epimerase to remove the toxic UDP-galactose that was accumulated in the cells in the presence of galactose. The other construction, pMOL1809 (SEQ ID NO:3) without a transcriptional terminator between the two genes showed some growth on TSS plates with galactose.

From these results it was clear that pMOL1807 (SEQ ID NO:2) had the potential to be used as an amplification unit in the presence of galactose.

The amplification procedure using galactose as the active agent can be performed in many different ways using both plates and broth cultures with different levels of galactose and other suger compounds or precursors from which free galactose can be released. We performed a number of different amplification procedures to evaluate their efficiency. The following table is a thorough description of the different amplification steps each transformant goes through before inoculation in a shakeflask (100 ml BPX). The Kan marker makes it possible to amplify by using Kan in the traditional way and then to compare the amplification efficiency to the galactose method of the invention.

TABLE 4

The table shows the amplification method of individual clones and the actual amylase yields from a 5 day fermentation in 100 ml SK1-M medium at 300 C. Some of the fermentations were performed in the presence pf galactose or Kan to select for multiple copies during the fermentations. From the table it is obvious that amplification protocols using Kan or galactose in TY full broth show the highest yields (in bold). These results show that yield improvements by adding galactose is as efficient as using Kan.

| # | Amplification method | KNU(T)/g |
|---|---|---|
| 1 | Transformant directly from LBPA | 2.54 |
| 2 | Transformant directly from LBPA | 2.16 |
| 3 | Transformant on LBPA, re-streaked 3x | 2.01 |
| 4 | MOL1815 (single copy transformant) | 3.63 |
| 5 | Transformant on LBPA >re-streaked on TSS + 0.2% ara + 0.5% gal | 5.09 |
| 6 | as #5 + 2% gal in shakeflask | 4.53 |
| 7 | Transformant on LBPA >2x (innoc. in liquid TSS + 0.2% ara + 0.5% gal) >2x (re-streaked on TSS + 0.2% ara + 0.5% gal) | 4.77 |
| 8 | as #8 + 0.5% gal in shakeflask | 5.66 |
| 9 | Transformant on LBPA >re-streaked on TSS + 0.2% ara + 0.5% gal >2x (innoc. in liquid TY + 0.5% gal) >2x (re-streaked on TSS + 0.2% ara + 0.5% gal) | 7.10 |
| 10 | as #9 + 0.5% gal in shakeflask | 2.09 |
| 11 | Transformant on LBPA >re-streaked on TSS + 0.2% ara + 0.5% gal >2x (innoc. in liquid TY + 0.5% gal) >2x (re-streaked on LBPA) | 6.70 |
| 12 | as #11 + 0.5% gal in shakeflask | 4.35 |
| 13 | Transformant on LBPA >re-streaked on TSS + 0.2% ara + 0.5% gal >2x (innoc. in liquid TY + 50 µg/ml Kan) >re-streaked on LBPA + 50 µg/ml Kan >re-streaked on LBPA | 7.71 |
| 14 | as #13 + 20 µg/ml Kan in shakeflask | 11.60 |
| 15 | as #9 | 6.65 |
| 16 | as #10 | 5.16 |
| 17 | as #11 | 12.10 |
| 18 | as #12 | 9.40 |
| 19 | as #13 | 7.10 |
| 20 | as #14 | 6.30 |
| 21 | Transformant on TSSA + 0.2% ara + 0.5% gal >2x (re-streaked on TSSA + 0.2% ara + 0.5% gal) | 4.30 |
| 22 | as #21 + 0.5% gal in shakeflask | 5.60 |
| 23 | as #21 | 2.90 |
| 24 | as #22 | 5.00 |
| 25 | Transformant on TSSA + 0.2% ara + 2% gal >2x (re-streaked on TSSA + 0.2% ara + 2% gal) | 3.60 |
| 26 | as #25 + 0.5% gal in shakeflask | 5.80 |
| 27 | as #25 | 5.00 |
| 28 | as #26 | 4.40 |

Southern Blot Analysis of Amplifications

Different clones from the fermentation studies shown in table 4 were subjected to a Southern blot analysis which confirmed that the high yields after Kan and galactose selection are results of amplification of the expression cassette. The Southern blot shows hybridization to flanking fragments of the dal locus and a strong hybridization band to the expression cassette corresponding to the size of the plasmid pMOL1807 (SEQ ID NO:2). The high intensity of the expression cassette hybridisation band in lanes 6–10 (FIG. 1) corresponds nicely to the high yields observed in the fermentation experiment in table 4 thus confirming that the yield increase correlates with expression cassette copy number.

The different strains were grown overnight in TY medium, and chromosomal DNA extracted by standard procedures (phenol/chloroform extractions). The DNA was digested with SphI, which cuts once within the integrated pMOL1807 (SEQ ID NO:2) plasmid. Fragments were transferred to Immobilon-N (Millipore) membranes after agarose electrophoresis by vacuum blotting, and the membrane probed with biotinylated labeled probes, using the NEBlot Phototope Kit and Phototope Detection Kit from New England Biolabs. Purified plasmid pMOL1807 (SEQ ID NO:2) was linearized with PstI restriction enzyme and used as probe for detection of the integrated plasmid (5943 bp) and flanking fragments of 4661 bp and 10851 bp.

A single copy insertion of the pMOL1807 (SEQ ID NO:2) plasmid in the dal locus will show only the two flanking bands of 4661 bp and 10851 bp while two or more copies of the integrated plasmid will show an additional band corresponding to the size of the plasmid itself.

The intensity of the plasmid sized band on the Southern blot will reflect the number of copies in the particular strain studied.

The Southern blot in FIG. 1 shows samples from different strains either amplified by use of galactose or kanamycine or strains where no selection pressure is opposed.

The results summarized herein show that it is indeed possible to increase the copy number of a chromosomally integrated expression cassette holding the galE gene by adding a simple suger compound such as galactose to the growth medium. The amplification potential, as judged from the band intensity on the Southern blots (FIG. 1) and the fermentation yields (table 4), is very similar to what can be achieved by the traditional kanamycine antibiotic selection/amplification.

What is claimed is:

1. A method for producing a polypeptide, comprising:

(a) culturing a bacterial host cell comprising two or more amplified copies of an amplification unit in the chromosome, said amplification unit comprising:

i) an expression cassette comprising at least one copy of a gene of interest encoding the polypeptide; and ii) at least one expressible copy of a chromosomal gene of the host cell encoding at least one enzyme involved in the removal of UDP-galactose from the bacterial cell when the cell is grown in the presence of galactose or a galactose precursor; and (b) recovering the polypeptide.

2. The method of claim 1, wherein the host cell is a Bacillus cell selected from the group consisting of *Bacillus*

*alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*.

3. The method of claim 1, wherein the at least one expressible copy of the chromosomal gene of step (a) encodes an enzyme selected from the group consisting of galactokinase (EC 2.7.1.6), UTP-dependent pyrophosphorylase (EC 2.7.7.10), UDP-glucose-dependent uridylyltransferase (EC 2.7.7.12), and UDP-galactose eplmerase (EC 5.1.2.3).

4. The method of claim 1, wherein the at least one expressible copy of the chromosomal gene of step (a) is galE.

5. The method of claim 1, wherein the galactose precursor is lactose, meliblose, raffinose, stechyos, verbascose or galactinol.

6. The method of claim 1, wherein th bacterial host cell is cultured in a medium comprising an enzyme capable of degrading the galactose precursor to produce free galactose.

7. The method of claim 1, wherein the amplification unit further comprises a nucleotide sequence with a homology to a chromosomal nucleotide sequence of the host cell sufficient to effect chromosomal integration in the host cell at the amplification unit by homologous recombination.

8. The method of claim 1, wherein the polypeptide is a hormone, a pro-hormone, a pre-pro-hormone, a small peptide, a receptor, or a neuropeptide.

9. The method of claim 1, wherein the hoot cell during the culturing step secretes an enzyme into the culture medium, which enzyme is capable of degrading the galactose precursor to produce free galactose.

10. The method of claim 9, wherein the secreted enzyme is a galactosidase.

11. The method of claim 1, wherein the amplification unit further comprises a nucleotide sequence of at least 100 bp with an identity of at least 70% to a chromosomal nucleotide sequence of the host cell.

12. The method of claim 11, wherein the nucleotide sequence comprised in the amplification unit is a partial non-functional copy of a conditionally essential gene of the host cell.

13. The method of claim 12, wherein the nucleotide sequence comprised in the amplification unit is a partial non-functional copy of a D-alanine racemase.

14. A method for constructing a bacterial hoot cell comprising two or more amplified copies of an amplification unit integrated into the host cell chromosome, wherein the method comprises the steps of:
  (a) providing a bacterial host cell wherein a chromosomal g ne encoding at least one enzyme involved in the removal or UDP-galactose is non-functional, whereby the host cell is susceptible to inhibition by UDP-galactose endogenously produced by the host cell when the host cell is cultivated in a medium comprising galactose or a galaclose precursor;
  (b) introducing a nucleic acid construct into the host cell of step (a), the construct comprising an amplification unit, and said amplification unit comprising:
    i) an expression cassette comprising at least one copy of a gene of interest; and
    ii) an expressible copy of the chromosomal gene of step (a) or a partial non-functional copy of the chromosomal gene of step (a),
  wherein at least one copy of the amplification unit integrates into the host cell chromosome;
  (c) cultivating the host cell of step (b) in a medium comprising galactose or a galactose precursor, wherein the at least one chromosomally integrated copy of the amplification unit is duplicated or multiplied on the host cell chromosome; and
  (d) selecting a host cell comprising two or more chromosomally integrated amplified copies of the amplification unit.

15. The method of claim 14 wherein the host cell is a Bacillus cell selected from the group consisting of *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringlensis*.

16. The method of claim 14, wherein the chromosomal gene of step (a) encodes an enzyme selected from the group consisting of galactokinase (EG 2.7.1.6). UTP-dependent pyrophosphorylase (EC 2.7.7.10), UDP-glucose-dependent undylyltransferase (EC 2.7.7.12), and UDP-galactose epimerase (EC 5.1.2.3).

17. The method of claim 14, wherein the chromosomal gene of step (a) is galE.

18. The method of claim 14, wherein the galactose precursor is lactose, melibiose, raffinose, stachyose, verbascose or galactinol.

19. Th method of claim 14, wherein the cultivating medium comprises an enzyme capabl of degrading the galactose precursor to produce free galactose.

20. The method of claim 14, wherein the nucleic acid construct is a plasmid.

21. The method of claim 14, wherein the amplification unit further comprises a nucleotide sequence with a homology to a chromosomal nucleotide sequence of the host cell sufficient to effect chromosomal integration in the host cell of the amplification unit by homologous recombination.

22. The method of claim 14, further comprising performing one or more additional cycles of steps (c) and (d) using th host cell selected in step (d) in each new cycle; wherein the number of chromosomally integrated amplified copies of the amplification unit increases with each cycle.

23. The method of claim 14, wherein the host cell secretes on enzyme into the medium which is capable of degrading the galactose precursor to produce free galactose.

24. The method of claim 23, wherein the secreted enzyme is a galactosidase.

25. The method of claim 14, wherein the nucleic acid construct further comprises an antibiotic selection marker flanked by resolvase sites or res-sites.

26. The method of claim 25, wherein a host cell comprising a first chromosomally integrated amplification unit is selected alter step (b), and the antibiotic marker excised from the host cell chromosome by a resolvase prior to performing step (c).

27. The method of claim 14, wherein the amplification unit further comprises a nucleotide sequence of at least 100 bp with an identity of at least 70% to a chromosomal nucleotide sequence of the host cell.

28. The method of claim 27, wherein the nucleotide sequence comprised in the amplification unit is a partial non-functional copy of a conditionally essential gene of the host cell.

29. The method of claim 28, wherein the conditionally essential gene encodes a D-alanine racemase.

30. A host cell produced by the method of claim 14.

* * * * *